(12) United States Patent
Adams et al.

(10) Patent No.: US 8,338,579 B2
(45) Date of Patent: Dec. 25, 2012

(54) HOMOGENEOUS ANALYTE DETECTION

(75) Inventors: Thomas Adams, Rancho Santa Fe, CA (US); Edward Jablonski, Escondido, CA (US)

(73) Assignee: Iris Molecular Diagnostics, Inc., Chatsworth, CA (US)

( * ) Notice: Subject to any disclaimer, the term of this patent is extended or adjusted under 35 U.S.C. 154(b) by 1255 days.

(21) Appl. No.: 11/718,379

(22) PCT Filed: Nov. 3, 2005

(86) PCT No.: PCT/US2005/040133
§ 371 (c)(1),
(2), (4) Date: Oct. 11, 2007

(87) PCT Pub. No.: WO2006/137932
PCT Pub. Date: Dec. 28, 2006

(65) Prior Publication Data
US 2008/0131883 A1    Jun. 5, 2008

Related U.S. Application Data

(60) Provisional application No. 60/624,950, filed on Nov. 3, 2004.

(51) Int. Cl.
*C07H 21/02* (2006.01)
*C07K 16/00* (2006.01)
*C12Q 1/68* (2006.01)
*G01N 33/566* (2006.01)

(52) U.S. Cl. .................. 536/23.1; 435/6.12; 530/391.1; 436/501

(58) Field of Classification Search .......................... None
See application file for complete search history.

(56) References Cited

U.S. PATENT DOCUMENTS

| | | | |
|---|---|---|---|
| 4,177,253 | A | 12/1979 | Davies et al. |
| 4,376,110 | A | 3/1983 | David et al. |
| 4,618,525 | A | 10/1986 | Chamberlain et al. |
| 4,824,776 | A | 4/1989 | Heller |
| 4,933,447 | A | 6/1990 | Koono |
| 4,946,778 | A | 8/1990 | Ladner et al. |
| 5,116,724 | A | 5/1992 | Delaage et al. |
| 5,270,184 | A | 12/1993 | Walker et al. |
| 5,501,983 | A | 3/1996 | Lilja et al. |

(Continued)

FOREIGN PATENT DOCUMENTS
EP    0359246 A2    3/1990
(Continued)

OTHER PUBLICATIONS

Niemeyer et al. Oligonucleotide-directed self-assembly of proteins: semisynthetic DNA-streptavidin hybrid molecules as connectors for the generation of macroscopic arrays and the construction of supramolecular bioconjugates. Nucleic Acids Research 22(25):5530-5539 (1994).*

(Continued)

*Primary Examiner* — Samuel Woolwine
(74) *Attorney, Agent, or Firm* — Duane Morris LLP

(57) ABSTRACT

The present invention provides novel binding pair compositions of defined and limited stability comprising nucleic acid detection markers useful for the homogeneous, sensitive detection of analytes. Also provided are methods for the sensitive homogeneous detection of analytes, particularly analytes of clinical relevance. Kits for preparing binding pairs of the invention and for performing the methods of the invention are also provided.

9 Claims, 8 Drawing Sheets

```
                                    15 BASE OVERLAP
[Antibody]-5' GCTACGGCTAGATCGTGTCCATGCGCTTACGACTTCGATGCTCGGCTCGCTAGCTAGATG 3'→ Direction of Extension                    [SEQ ID NO.:1]
                                  3' GAGCGATCGATCTACTACTTAGAGAGCATAGTATTCTTGTACCGCAACTTCTCAACCTCT 5' [SEQ ID NO.:3]
                                /
              [Antibody]- Spacer(s)
```

U.S. PATENT DOCUMENTS

| | | | |
|---|---|---|---|
| 5,599,677 | A | 2/1997 | Dowell et al. |
| 5,635,602 | A | 6/1997 | Cantor et al. |
| 5,648,213 | A | 7/1997 | Reddy et al. |
| 5,665,539 | A | 9/1997 | Sano et al. |
| 5,702,896 | A | 12/1997 | Collins et al. |
| 5,749,925 | A | 5/1998 | Bocker |
| 5,759,773 | A | 6/1998 | Tyagi et al. |
| 5,766,849 | A | 6/1998 | McDonough et al. |
| 5,789,165 | A | 8/1998 | Oku et al. |
| 5,849,878 | A | 12/1998 | Cantor et al. |
| 5,888,834 | A | 3/1999 | Ishikawa et al. |
| 5,985,548 | A | 11/1999 | Collier et al. |
| 6,086,540 | A | 7/2000 | Bonneville et al. |
| 6,165,942 | A | 12/2000 | Satow |
| 6,172,208 | B1 | 1/2001 | Cook |
| 6,193,953 | B1 | 2/2001 | Lohrmann et al. |
| 6,214,566 | B1 | 4/2001 | Asa et al. |
| 6,245,318 | B1 | 6/2001 | Klibanov et al. |
| 6,511,809 | B2 | 1/2003 | Baez et al. |
| 6,531,278 | B1 | 3/2003 | Weimer |
| 6,723,303 | B1 | 4/2004 | Quay |
| 7,649,001 | B2 | 1/2010 | Shiraishi |
| 7,932,060 | B2 * | 4/2011 | Nadeau et al. ............... 435/91.2 |
| 2002/0064779 | A1 | 5/2002 | Landegren et al. |
| 2003/0104359 | A1 | 6/2003 | Cuthbertson et al. |
| 2003/0138432 | A1 * | 7/2003 | Glazier ..................... 424/178.1 |
| 2004/0142323 | A1 * | 7/2004 | Caine Boyde ................... 435/6 |
| 2005/0026161 | A1 | 2/2005 | Jablonski |
| 2005/0170398 | A1 * | 8/2005 | Van Berkel et al. .............. 435/6 |
| 2009/0176207 | A1 | 7/2009 | Neuman |
| 2009/0246781 | A1 | 10/2009 | Adams et al. |

FOREIGN PATENT DOCUMENTS

| | | | |
|---|---|---|---|
| EP | 0359246 | A3 | 3/1990 |
| EP | 0488152 | | 6/1992 |
| EP | 1249500 | A | 10/2002 |
| GB | 2091729 | | 8/1982 |
| WO | WO 92/16841 | | 10/1992 |
| WO | WO 93/07883 | | 4/1993 |
| WO | WO 96/15130 | | 5/1996 |
| WO | WO 97/04466 | A1 | 1/1997 |
| WO | WO 9700446 | A1 * | 1/1997 |
| WO | WO 97/40049 | | 10/1997 |
| WO | WO 98/53857 | | 12/1998 |
| WO | WO 00/41524 | | 7/2000 |
| WO | WO 01/96608 | | 12/2001 |
| WO | WO 02/068695 | | 9/2002 |
| WO | WO 02/083951 | | 10/2002 |
| WO | WO 03/011824 | | 2/2003 |
| WO | WO 03076943 | A1 * | 9/2003 |
| WO | WO 2004/042030 | | 5/2004 |
| WO | WO 2006/034441 | | 3/2006 |
| WO | WO 2006/137933 | | 12/2006 |
| WO | WO 2009/105264 | | 8/2009 |

OTHER PUBLICATIONS

DeLisi, C. Detection and analysis of recognition and selection in the immune response. Bulletin of Mathematical Biology 39:705-719 (1977).*
Bazemore et al. Kinetic analysis of pairing and strand exchange catalyzed by RecA. J. Biol. Chem. 272(23):14672-14682 (1997).*
Molecular Probes Anti-Fluorescein Antibodies Product Information (Feb. 2001).*
Molecular Probes Anti-Tetramethylrhodamine Antibodies Product Information (Feb. 2001).*
Non Final Office Action, U.S. Appl. No. 10/701,347, Mail Date Nov. 23, 2010.
In re European Patent Application No. 03 810 829.6-1223, Communication Pursuant to Article 94(3) EPC, Dated Mar. 4, 2008.
In re European Patent Application No. 03 810 829.6-1223, Supplementary European Search Report, Dated Nov. 28, 2006.
In re European Patent Application No. 03 810 829.6-1223, Communication Pursuant to Article 94(3) EPC, Dated Sep. 28, 2009.
In re European Patent Application No. 03 810 829.6-1223, Communication Pursuant to Article 94(3) EPC, Dated Aug. 31, 2010.
In re European Patent Application 05858303.0, Supplementary Search Report, Dated Jul. 8, 2009.
In re European Patent Application 05858303.0, European Search Report, Dated Jul. 8, 2009.
In re European Patent Application 05858303.0, Communication According to Article 94(3) EPC, Dated Oct. 2, 2009.
In re Australian Patent Application No. 2005333156, Examiner's First Report, Dated May 4, 2010.
PCT International Search Report for foreign counterpart International Application No. PCT/US09/1114.
PCT International Preliminary Report from counterpart International Application No. PCT/US03/35153, Sep. 18, 2007.
Supplemental Search Report from counterpart EP Application No. 03810829.6, Nov. 20, 2006.
Supplemental Search Report from counterpart EP 05858304 dated Aug. 8, 2008.
PCT International Search Report for foreign counterpart International Application No. PCT/US03/35153, Aug. 31, 2004.
In re Chinese Patent Application No. 200580038082.8, Examiner's First Report, Dated Dec. 11, 2009.
In re European Patent Application No. 05858304.8, Supplementary Search Opinion, Dated Aug. 12, 2008.
In re European Patent Application 05858304.8, Communication According to Article 94(3) EPC, Dated Nov. 10, 2008.
In re European Patent Application 05858304.8, Communication According to Article 94(3) EPC, Dated Sep. 4, 2009.
In re European Patent Application 05858304.8, Annex to Communication Dated Dec. 28, 2009.
In re European Patent Application 05858304.8, Annex to Communication Dated Jun. 1, 2010.
In re European Patent Application 05858304.8, Annex to Communication Apr. 14, 2010.
In re Australian Patent Application No. 2005333157, Examiner's First Report, Dated Jun. 2, 2010.
International Search Report for foreign counterpart International Application No. PCT/US2009/001114 Dated Jun. 22, 2009.
Written Opinion for foreign counterpart International Application No. PCT/US2009/001114 Dated Jun. 22, 2009.
International Search Report from counterpart International Application No. PCT/US05/040162, Dated Feb. 16, 2007.
International Report on Patentability from counterpart International Application No. PCT/US05/040162, Dated May 8, 2007.
International Search Report from counterpart International Application No. PCT/US2005/040133.
International Preliminary Report on Patentability from counterpart International Application No. PCT/US2005/040133.
Final Office Action, U.S. Appl. No. 10/701,347, Mail Date Mar. 17, 2008.
Non Final Office Action, U.S. Appl. No. 10/701,347, Mail Date Jul. 24, 2007.
Non Final Office Action, U.S. Appl. No. 10/701,347, Mail Date Sep. 22, 2006.
Barletta, et al. Expert Opinion Med. Diagn. 1:(2):267-288 (2007).
Bird, Science, 242:423-26 (1998).
Boyle et al. Annals of Oncology 16:481-488 (2005).
Cookson et al. J. Urology 177(2):540-545.
Cote et al., Proc. Natl. Acad. Sci. USA, 80:2026-30 (1983).
Diamandis, et al. Journal of Urology 157(3): 913-918 (Mar. 1997).
Doherty et al. Br. J. Cancer 83(11):1432-1436 (2000).
Ellis et al. Adult Urology 50(4):573-579 (1997).
Furuya et al. J. Immunol. Methods, 238:173-180, 2000.
Hendrickson et al. Nucleic Acids Res., 1995, 23:522-529.
Hermanson, Bioconjugate Techniques, pp. 639-666, 1996.
Holmberg, et al. Surfactant—Protein Mixtures Ch. 14.
Hombach et al. EMBO 7(11) pp. 3451-3456 (1988).
Huse et al. Science, 246:1275-81 (1989).
Huston et al. Proc. Natl. Acad. Sci. USA, 85:5879-83 (1988).
Jablonski, Ed and Adams, Tom (IVDT, Nov. 2006, p. 63). Category: Molecular Diagnostics. Keywords: New Technology.
Jablonski et al. Nucl. Acids Res. 14:6115-28 (1986).
Jablonski, et al. Clinical Chemistry 53(6S): A108-A109 (Jul. 15, 2007).
Joerger et al., Clin chem 41/9: 1371-1377, 1995.

Junker et al. Anticancer Research 19:2625-2658 (1999).
Klee et al. Adult Urology 44(1): 76-82 (Jul. 1994).
Kohler and Milstein, Nature, 256:495-7.
Lindner et al., Journal of Nuclear Cardiology 11(2):215-221, especially Figure 1 (2004).
McKie et al., J. Immunol. Meth., 2002, 261:167175.
Manetti et al. J. Endocrinol. Invest. vol. 25 pp. RC29-RC31 (2002).
McCarthy, D. Flow Cytometry: Principles and Applications, Edited by M.G. Macey Chapter 2.
Morrison, et al., Proc. Natl. Acad. Scie., 81:6851-6855 (1984).
Morrissey et al., Anal Biochem., 1989, 181:345-359.
Moul, J. Urology 163:1632-42 (2000).
Niemeyer et al., Analytical Biochemistry, Academic Press, San Diego, CA vol. 268, No. 1 (Mar. 1, 19999), pp. 54-63.
Nilsson et al. Acta Oncologica 43(4):316-381 (2004).
Otzen, et al. Biophysical Journal 83:2219-2230, Oct. 2002.
Prott, et al. AntiCancer Research 23:979-982 (2003).
Ramsby et al. Preparation of Cellular and Subcellur Extracts Ch. 3.
Sano et al. Science, 1992, 258:120-22.
Saito, et al., Clin. Chem. 45:5:665-669 (1999).
Schick et al. Journal of Immunology 151(8):4090-4097 (Oct. 15, 1993).
Seto, et al. Luminescence 16:285-290 (2002).
Stamey, Clin. Chem. 42(6)849-852.
Sugawara et al. Clint Chem. Act, 299:45-54, 2000.
Takeda et al., Nature, 314:452-54 (1985).
Taylor et al. Journal Compilation vol. 98 pp. 540-543 (2008).
Trock et al. ASCO Urogenitary Cancers Symposium, Abstract No. 85.
Tsutsui et al., Cardiovascular Ultrasound 2004 2(23):1-7, especially pp. 1-2 (2004).
Tyagi and Kramer, Nt. Bitechnol., 1996, 14:303-308.
Tyagi et al., Nat. Biotechnol., 2000, 18:1191-96.
UK Prostate Cancer incidence statistics, http://info.cancer-researchuk.org/cancerstats/types/prostate/incidence/ (last accessed Jan. 27, 2009).
Vassilikos et al. Clinical Biochemistry 33(2):115-123 (2000).
Vaisanen et al. Prostate Cancer and Prostatic Disease 2:91-97 (1999).
Walker, Science., 296:557-58 (2002).
Ward et al. Nature, 334:544-46 (1989).
Weller et al. Proceedings of $2^{nd}$ hoint EMBS/BMES Conference, Houston, TX, Oct. 23-26, 2002, especially p. 897.
Witherspoon et al. The Journal of Urology 157:1322-1328 Apr. 1997.
In re European Patent Application 09713301.1-1223, Communication pursuant to Article 94(3), Dated Jan. 18, 2011.
Extended Search Report form counterpart European Patent Application No. 10190637.8, Dated Feb. 28, 2011.
Partial European Search Report form counterpart European Patent Application No. 10184768.9.
Non Final Office Action, U.S. Appl. No. 11/718,090, Mail Date Mar. 1, 2011.
Hirn-Scavennec, et al., Transplantation 46(4) pp. 558-563 (Oct. 1988).
In re Chinese Patent Application No. 200580038082.8, Examiner's Second Report, Dated Aug. 24, 2011.
European Search Report from counterpart European Patent Application No. 10190637.8, Date Feb. 21, 2011.
Extended Search Report from counterpart European Patent Application No. 10184768.9, Date Apr. 27, 2011.
Non Final Office Action, U.S. Appl. No. 11/718,090, Mail Date May 20, 2011.
Non Final Office Action, U.S. Appl. No. 12/378,965, Mail Date Sep. 28, 2011.
Jeanene Swanson; "The Rise of ImmunoPCR"; GenomeWeb, Aug. 30, 2007; pp. 1-4.
Kilbanov, Alexander; "Targeted delivery of gas-filled microspheres, contrast agents for ultrasound imagining"; Advance Drug Delivery Reviews, 1999, vol. 37; pp. 139-157.
Lind et ai, J Immunological Mehtods 304:107-116,2005.
Means G E et al: "Chemical Modifications 6 of Proteins: History and Applications", Bioconjugate Chemistry, ACS, Washington, DC, US, vol. 1, No. 1, Jan. 1, 1990, pp. 2-12, Xp000236570.
Patel et al (Adult Urology, 65:942-946, 2005.
William Check, PhD, "PCR and ELISA adaptations—will they fly?"; College of American Pathologist Journal; Jul. 2007; 6 pages.

* cited by examiner

5' NH3-C12-GCTACGGCTAGATCGTGTCCATGCGCTTACGACTTCGATGCTCGGCTAGCTAGATG-3' [SEQ ID NO.:1]
              |||||||||||||||||||||||||||||||||||||||||||||||||||
3'-GAGCGGATCGATCTACTAGCTTAGAGAGCATAGTATTCTTGTACCGAACTTCTCAACCTCT-C12-NH3-5' [SEQ ID NO.:3]

↓

5' NH3-C12-GCTACGGCTAGATCGTGTCCATGCGCTTACGACTTCGATGCTCGGCTAGCTAGATG-3'------→ Extension from 3' OH
              ||||||||||||||||||||||||||||||||||||||||||||||||||||
           ←------ Extension from 3' OH 3'-GAGCGGATCGATCTACTAGCTTAGAGAGCATAGTATTCTTGTACCGAACTTCTCAACCTCT-C12-NH3-5'

↓ binding site for primer 5 [SEQ ID NO. 5]
5' NH3-C12-GCTACGGCTAGATCGTGTCCATGCGCTTACGACTTCGATGCTCGGCTAGCTAGATGATGAATCTCTGCTATCATAAGAACATGGCGTTGAAGAGTTGAGA
CGATGCCGATCTAGCACAGGTACGCACAGCGAATGCTACGGCTGAAGCTACGAGCGATCGATCTACTACTTAGAGAGCATAGTATTCTTGTACCGAACTTCTCAACCTCT -C12-NH3-5'
Binding site for primer 4
[SEQ ID NO.:4]

FIG. 3

Real-Time PCR of 9 and 15 base pair overlapping DNA strands.

```
                                    15 BASE OVERLAP
[Antibody]-5' GCTACGGCTAGATCGTGTCCATGCGCTTACGACTTCGATGCTCGGCTCGGCTAGCTAGATG 3' → Direction of Extension         [SEQ ID NO.:1]
                                 3' GAGCGATCGATCTACTACTTAGAGACGATAGTATTCTTGTACCGCAACTTCTCAACCTCT 5' [SEQ ID NO.:3]
                                   /
                    [Antibody]- Spacer(s)
```

FIG. 6

HOMOGENEOUS ANALYTE DETECTION

RELATED APPLICATIONS

This application is a 371 of International Application No. PCT/US2005/040133, filed Nov. 3, 2005, which claims priority from Provisional Application No. 60/624,950, filed Nov. 3, 2004, the entire disclosures of which are hereby incorporated by reference in their entirety.

FIELD OF THE INVENTION

This invention relates to methods, compositions and kits for determining the presence or concentration of an analyte in a sample.

BACKGROUND OF THE INVENTION

There is a desire in the field of clinical chemistry to determine the concentrations of proteins, drugs, organisms and other analytes in biological fluids for the purpose of diagnosing and monitoring disease. For example, during myocardial infarction proteins are released from the heart. Detecting the presence, concentration and time course of release of such proteins can aid in the diagnosis of a heart attack.

Most clinically relevant proteins that are currently detected in biological fluids are present at concentrations greater than 1 picogram/ml. Prostate specific antigen (PSA), for example, is a serum protein useful in the detection of prostate disease that is normally present in males at concentrations of about 0-4 ng/ml. PSA levels above 4 ng/ml are suspicious for prostate disease, particularly prostate cancer. This concentration range is readily detected by conventional immunoassay technology. Following prostate removal, however, the concentration of PSA drops to levels that are undetectable by conventional technology. Increasing PSA levels in cancer patients that have undergone prostate removal is indicative of relapse. An assay with femtogram/ml sensitivity is required to monitor these patients.

It is estimated that there are approximately 35,000 genes and as many as 500,000 proteins in the human species. The increased diversity of proteins versus genes can be accounted for post transcriptional (e.g., splicing) and posttranslational (e.g., phosphorylation, glycosylation) modifications. Such modifications can significantly alter protein function. Thus, even subtle differences may be clinically relevant. Only 290 proteins have been identified in human plasma even though there are thousands of spots seen in 2D gels. The human plasma proteome may contain hundreds of thousands of proteins that are present at concentrations too low to detect by current technology. Methods to detect the majority of these proteins are not currently available.

The difficulty of detecting low concentrations of certain analytes is compounded by the relatively small sample sizes that can be utilized in a clinical assay. Therefore, most immunoassays for protein analytes rely on heterogeneous methodology such as ELISA (enzyme linked immunosorbent assay), in which antibody-bound analyte is physically separated from unbound analyte. Heterogeneous detection methods are complicated and require multiple steps (e.g., binding to a solid phase and repeated washing steps) to separate the bound analyte from the unbound. These steps lead to non-specific binding and lowered sensitivity; they can be costly and time consuming. Thus, there is a need for a high sensitivity homogenous assay which avoid non-specific binding.

Homogeneous immunoassays (those which do not require a physical separation of the bound-species and the free-species) have been described for small molecules, such as drugs. These assays include SYVA's FRAT® assay, EMIT® assay, enzyme channeling immunoassay, and fluorescence energy transfer immunoassay (FETI) (Dade Behring, Deerfield, Ill.); enzyme inhibitor immunoassays (Hoffman LaRoche and Abbott Laboratories): fluorescence polarization immunoassay (Dandlicker), among others. All of these methods have limited sensitivity, and only a few, including FETI and enzyme channeling, are suitable for large multiepitopic analytes. Thus, there exists a need for a sensitive, homogeneous method for the detection of large and/or complex analytes present in biological and clinical samples.

SUMMARY OF THE INVENTION

The present invention provides a binding pair having a first binding member comprising a first specificity molecule coupled to a first nucleic acid, and a second binding member comprising a second specificity molecule coupled to a second nucleic acid, where the first and second nucleic acids form a duplex of defined and limited stability.

In certain embodiments, the first and second specificity molecules may be receptors, ligands, or antibodies. The specificity molecules may be identical or different from each other. In one embodiment, the specificity molecules of the present invention interact with two receptors on a single cell. In another embodiment, both the first and second specificity molecules are monoclonal antibodies, which may interact with different epitopes on the same antigen and thereby comprise a sandwich pair.

The first and second nucleic acids of the binding pairs are typically single-strand nucleic acids which may be DNA, RNA, or PNA, but may be partially double-stranded nucleic acids or analogues thereof. In certain embodiments of the invention, at least one of the nucleic acids is a chimeric DNA/RNA molecule. The nucleic acids of the invention may be coupled via their 5' ends or their 3' ends. In one aspect of the invention, one nucleic acid of a binding pair is coupled via its 5' end and the other via its 3' end. The duplex between the nucleic acids may be formed between terminal ends of the nucleic acids or may comprise an internal nucleic acid sequence. In a preferred embodiment, the nucleic acid is suitable for amplification by PCR, LCR, SDA, or TMA.

The present invention also provides methods for detecting an analyte using binding members. According to one embodiment, a binding pair, as described above, is contacted with an analyte to form a complex. The binding pair nucleic acid is then dissociated and then re-associated. Following extension of the 3' ends of the reformed duplex, which is found predominantly in analyte-bound binding pairs, the reformed duplex may be detected, typically by amplifying a nucleic acid comprising the duplex by PCR. Background can be reduced significantly when the PCR primers bind only to sites generated by extending the 3' ends of the reformed duplex but not to the nucleic acids of the binding members themselves.

The amplification products can be detected by any one of a variety of methods including staining with ethidium bromide, silver staining, autoradiography, dot blotting, slot blotting, southern blotting, and incorporation of a fluorescent molecule, a fluorescence quencher molecule, a chemiluminescent compound, a chemiluminescence quencher molecule, a bioluminescent compound or a fluorescent nucleotide.

In one embodiment of the invention, one of the binding pair nucleic acids is a chimeric DNA/RNA molecule and the other is a DNA molecule, where the duplex formed between the two nucleic acids has a short DNA/DNA hybrid region and longer DNA/RNA hybrid region. The intact duplex of this embodiment is stable, but can be destabilized by digestion with RNAse, which further reduces the background due to binding members that are not bound to analyte.

The various embodiments of the invention can be combined to create a homogenous assay for detection of clinically relevant proteins, viruses and cells that is both specific and highly sensitive.

BRIEF DESCRIPTION OF THE DRAWINGS

FIG. 3 provides a general scheme for duplex formation, 3' extension and PCR amplification of a nucleic acid pair comprising SEQ ID NO.:1 and SEQ ID NO.:3.

FIG. 6 shows the orientation and duplex formation of a nucleic acid pair where one of the oligonucleotides [SEQ ID NO.:1] is attached via a spacer attached to its 3' end and the other oligonucleotide SEQ ID NO.:3] is attached directly via its 5' end.

DETAILED DESCRIPTION OF THE INVENTION

Figure 1:
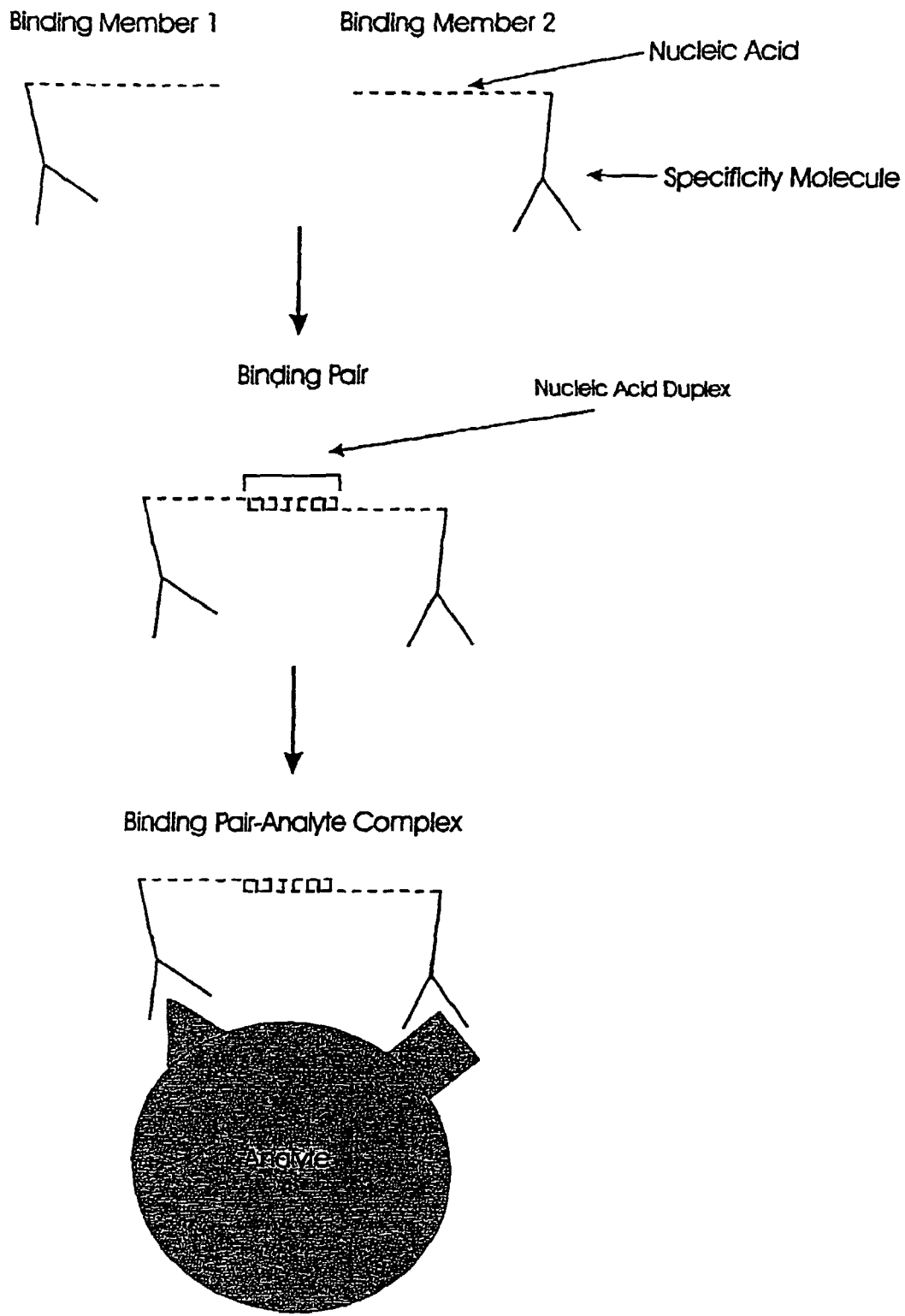
FIG. 1 illustrates the content, conformation and general binding scheme for binding pairs.

If is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

DEFINITIONS

Before proceeding further with a description of the specific embodiments of the present invention, a number of terms will be defined and described in detail.

Unless specific definitions are provided, the nomenclature utilized in connection with, and the laboratory procedures, techniques and methods described herein are those known in the art to which they pertain. Standard chemical symbols and abbreviations are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, delivery, and treatment of patients. Standard techniques may be used for recombinant DNA methodology, oligonucleotide synthesis, tissue culture and the like. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), Harlow & Lane, *Antibodies: A Laboratory Manual* (Cold Spring Harbor Laboratory Press, Cold Spring Harbor, N.Y. (1988)), which are incorporated herein by reference in their entirety for any purpose.

"Binding member" as used herein, refers to a conjugate formed between a specificity molecule and a nucleic acid. Compositions containing two binding members linked by a duplex of defined and limited stability formed between the binding member nucleic acids are referred to as "binding pairs." Binding pairs combine with an analyte to form a binding pair-analyte complex which is herein referred to simply as a "complex."

The term "analyte," as used herein, refers to any substance that it is desirable to detect in an assay, and which may be present in a sample. The analyte can be, without limitation, any substance. In a preferred embodiment of the invention, an analyte comprises a substance for which there exists a naturally occurring antibody or for which an antibody can be prepared. The analyte may be, for example, a protein, a polypeptide, a hapten, a carbohydrate, a lipid, a drug, a cell or any other of a wide variety of biological or non-biological molecules, complexes or combinations thereof. In another embodiment, the analyte is a nucleic acid. In still another embodiment the analyte is an antibody. In yet another embodiment, the analyte is a cell (animal, plant, fungal, bacterial, etc.) or a subcomponent or organelle (e.g., mitochondria) thereof.

Polyvalent ligand analytes that can be detected using compositions, methods and kits of the present invention will normally be poly(amino acids), i.e., polypeptides, proteins, polysaccharides, nucleic acids, and combinations thereof. Such combinations include components of cells, tissues, bacteria, viruses, cell walls, cell membranes, cellular organelles, chromosomes, genes, mitochondria, nuclei and the like. According to one aspect of the invention, certain analytes do not contain nucleic acid.

A wide variety of protein analytes may be advantageously detected using the methods of the present invention. Such protein analytes can be classified according to family, with each family having similar structural features, biological functions, relationship to specific microorganisms (particularly disease causing microorganisms), and the like. Protein families of particular interest for the present invention include, for example, immunoglobulins, cytokines, enzymes, hormones, cancer antigens, nutritional markers, tissue specific antigens, and biowarfare agents. These protein analytes may be present in blood, serum, plasma, spinal fluid, synovial fluid, saliva, urine, cells or tissues.

The following are examples of classes of protein analytes related by structure that may be detected using the compositions, methods and kits of the present invention:

protamines
histones
albumins globulins
scleroproteins
phosphoproteins
mucoproteins The following examples are clinically important proteins found in human plasma that may be detected using the compositions, methods and kits of the present invention:
$\alpha_1$-Lipoprotein
$\alpha$1-Antitrypsin
Transcortin
4.6S-Postalbumin
Tryptophan-poor
$\alpha_1$-Glycoprotein
$\alpha_{1x}$-Glycoprotein
Thyroxin-binding globulin
Inter-$\alpha$-trypsin-inhibitor
Gc-globulin
   (Gc 1-1)
   (Gc 2-1)
   (Gc 2-2)
Haptoglobin
   (Hp 1-1)
   (Hp 2-1)
   (Hp 2-2)
Ceruloplasmin
Cholinesterase
$\alpha$2-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\gamma_2$-glycoprotein I
$\gamma_2$-glycoprotein II
Immunoglobulin G
(IgG) or $\gamma$G-globulin
   Mol. formula: $\gamma 2k2$ or $\beta 2\lambda 2$
Immunoglobulin A (IgA) or $\gamma$A-globulin
   Mol. formula: $(\alpha_2\kappa_2)^n$ or $(\alpha_2\kappa_2)^n$
Immunoglobulin M (IgM) or $\gamma$M-globulin
   Mol. formula: $(\mu_2\kappa_2)^5$ or $(\mu_2\lambda_2)^5$
Immunoglobulin D (IgD) or $\gamma$D-Globulin ($\gamma$D)
   Mol. formula: $(.delta._2\kappa_2)$ or $(.delta._2\lambda_2)$
Immunoglobulin E (IgE) or $\gamma$E-Globulin ($\gamma$E)
   Mol. formula: $(\epsilon_2\kappa_2)$ or $(\epsilon_2\lambda_2)$
Free $\kappa$ and $\lambda$ light chains
Complement factors:
  C'1
  C'1q
  C'1r
  C'1s
  C'2
  C'3
  $\beta_1$A
  $\alpha_2$D
  C'4
  C'5
  C'6
  C'7
  C'8
  C'9

Important blood clotting factors that may be detected using the compositions, methods and kits of the present invention include the examples listed in the Table below.

TABLE 1

BLOOD CLOTTING FACTORS

| International Designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin |
| XIII | Fibrin-stabilizing factor |

Important protein hormones that may be detected using the compositions, methods and kits of the present invention include:
   Peptide and Protein Hormones
   Parathyroid hormone (parathromone)
   Thyrocalcitonin
   Insulin
   Glucagon
   Relaxin
   Erythropoietin
   Melanotropin (melanocyte-stimulating hormone; intermedin)
   Somatotropin (growth hormone)
   Corticotropin (adrenocorticotropic hormone)
   Thyrotropin
   Follicle-stimulating hormone
   Luteinizing hormone (interstitial cell-stimulating hormone)
   Luteomammotropic hormone (luteotropin, prolactin
   Gonadotropin (chorionic gonadotropin)
   Tissue Hormones
   Secretin
   Gastrin
   Angiotensin I and II
   Bradykinin
   Human placental lactogen
   Cytokines
   IL 1
   IL 2
   IL 4
   IL 6
   IL 8
   IL10
   EGF
   TNF
   NGF
   Cancer Antigens
   PSA
   CEA
   $\alpha$-fetoprotein
   Acid phosphatase
   CA19.9
   CA125
   Tissue Specific Antigens
   alkaline phosphatase
   myoglobin CPK-MB
Troponin
BNP
Pro-BNP
Calcitonin
Myelin basic protein
Peptide Hormones from the Neurohypophysis
Oxytocin
Vasopressin
Releasing factors (RF) CRF, LRF, TRF, Somatotropin-RF, GRF, FSH-RF, PIF, MIF
Ricin
Diptheria toxin
Botulism toxin
*Staphylococcus* enterotoxin B Bacteria and viruses are also analytes that may be detected using the compositions, methods and kits of the present invention. Included among these biological analytes are, among others:

Corynebacteria
*Corynebacterium diphtheria*
Pneumococci
*Diplococcus pneumoniae*
Streptococci
*Streptococcus pyrogenes*
*Streptococcus salivarus*
Staphylococci
*Staphylococcus aureus*
*Staphylococcus albus*
Neisseria
*Neisseria meningitidis*
*Neisseria gonorrhea*
Enterobacteriaciae
Coliform
*Escherichia coli*
*Aerobacter aerogenes*
*Klebsiella pneumoniae*
Salmonellae
*Salmonella typhosa*
*Salmonella choleraesuis*
*Salmonella typhimurium*
Shigellae
*Shigella dysenteria*
*Shigella schmitzii*
*Shigella arabinotard*
*Shigella flexneri*
*Shigella boydii*
*Shigella sonnei*
Other Enteric Bacilli
*Proteus vulgaris*
*Proteus mirabilis*
*Proteus* species
*Proteus morgani*
*Pseudomonas aeruginosa*
*Alcaligenes faecalis*
*Vibrio cholerae*
*Hemophilus-Bordetella* Group
*Hemophilus influenza,*
*Hemophilus ducryi*
*Hemophilus hemophilus*
*Hemophilus aegypticus*
*Hemophilus parainfluenza*
*Bordetalla pertussis*
Pasteurellae
*Pasteurella pestis*
*Pasteurella tulareusis*
Brucellae
*Brucella melitensis*
*Brucella abortus*
*Brucella suis*
Aerobic Spore-forming Bacilli
*Bacillus anthracis*
*Bacillus subtilis*
*Bacillus megaterium*
*Bacillus cereus*
Anaerobic Spore-Forming Bacilli
*Clostridium botulinum*
*Clostridium tetani*
*Clostridium perfringens*
*Clostridium novyi*
*Clostridium septicum*
*Clostridium histolyticum*
*Clostridium tertium*
*Clostridium bifermentans*
*Clostridium sporogenes*
Mycobacteria
*Mycobacterium tuberculosis hominis*
*Mycobacterium bovis*
*Mycobacterium avium*
*Mycobacterium leprae*
*Mycobacterium paratuberculosis*
Actinomycetes (Fungus-Like Bacteria)
*Actinomyces Isaeli*
*Actinomyces bovis*
*Actinomyces naeslundii*
*Nocardia asteroides*
*Nocardia brasiliensis*
The Spirochetes
*Treponema pallidum*
*Treponema pertenue*
*Treponema carateum*
*Borrelia recurrentis*
*Leptospira icterohemorrhagiae*
*Leptospira canicola*
Trypanasomes
Mycoplasmas
*Mycoplasma pneumoniae*
Other Pathogens
Rickettsiae (Bacteria-Like Parasites)
*Rickettsia prowazekii*
*Rickettsia mooseri*
*Rickettsia rickettsii*
*Rickettsia conori*
*Rickettsia australis*
*Rickettsia sibiricus*
*Rickettsia akari*
*Rickettsia tsutsugamushi*
*Chlamydia* (Unclassifiable Parasites Bacterial/Viral)
*Chlamydia* Agents (Naming Uncertain)
Fungi
*Cryptococcus neoformans*
*Blastomyces dermatidis*
*Hisoplasma capsulatum*
*Coccidioides immitis*
*Paracoccidioides brasiliensis*
*Candida albicans*
*Aspergillus fumigatus*
*Mucor corymbifer* (*Absidia corymbifera*)
*Rhizopus oryzae*
*Rhizopus arrhizua*
*Phycomycetes*
*Rhizopus nigricans*
*Sporotrichum schenkii*

*Flonsecaea pedrosoi*
*Fonsecacea compact*
*Fonsecacea dermatidis*
*Cladosporium carrionii*
*Phialophora verrucosa*
*Aspergillus nidulans*
*Madurella mycetomi*
*Madurella grisea*
*Allescheria boydii*
*Phialophora jeanselmei*
*Microsporum gypseum*
*Trichophyton mentagrophytes*
*Keratinomyces ajelloi*
*Microsporum canis*
*Microsporum adouini*
*Trichophyton rubrum*
Viruses
  Adenoviruses
  Herpes Viruses
  Herpes simplex
  Varicella (Chicken pox)
  Herpes Zoster (Shingles)
  Virus B
  Cytomegalovirus
  Pox Viruses
  Variola (smallpox)
  Vaccinia
  Poxvirus bovis
  Paravaccinia
  Molluscum contagiosum
  Picornaviruses
  Poliovirus
  Coxsackievirus
  Echoviruses
  Rhinoviruses
  Myxoviruses
  Parainfluenza (1-4)
  Mumps Virus
  Newcastle Disease Virus
  Measles Virus
  Rinderpest Virus
  Canine Distemper Virus
  Respiratory Syncytial Virus
  Rubella Virus
  Arboviruses
  Eastern Equine Encephalitis Virus
  Western Equine Encephalitis Virus
  Sindbis Virus
  Chikugunya Virus
  Semliki Forest Virus
  Mayora Virus
  St. Louis Encephalitis Virus
  *Rickettsia prowazekii*
  California Encephalitis Virus
  Colorado Tick Fever Virus
  Yellow Fever Virus
  Dengue Virus
  Reoviruses
  Reovirus Types 1-3
  Retroviruses
  Human Immunodeficiency Viruses I and II (HIV)
  Human T-cell Lymphotrophic Virus I & II (HTLV)
  Hepatitis
  Hepatitis A Virus
  Hepatitis B Virus
  Hepatitis C Virus
  Tumor Viruses
  Rauscher Leukemia Virus
  Gross Virus
  Maloney Leukemia Virus
  Human Papilloma Virus In addition, it may be desirable to detect the normal or diseased tissue or cells of a patient. The presence or absence of certain circulating cancer or other cells, for example, may be diagnostic for disease. Thus, the endogenous cells of a human patient are analytes that may be advantageously detected using the compositions, methods and kits of the present invention.

The term "sample" as used herein refers to an aliquot of material, frequently an aqueous solution or an aqueous suspension derived from biological material. Samples to be assayed for the presence of an analyte by the methods of the present invention include, for example, cells, tissues, homogenates, lysates, extracts, purified or partially purified proteins and other biological molecules and mixtures thereof. Nonlimiting examples of samples typically used in the methods of the invention include human and animal body fluids such as whole blood, serum, plasma, cerebrospinal fluid, sputum, bronchial washings, bronchial aspirates, urine, lymph fluids and various external secretions of the respiratory, intestinal and genitourinary tracts, tears, saliva, milk, white blood cells, myelomas and the like; biological fluids such as cell culture supernatants; tissue specimens which may or may not be fixed; and cell specimens which may or may not be fixed.

The samples used in the methods of the present invention will vary based on the assay format and the nature of the tissues, cells, extracts or other materials, especially biological materials, to be assayed. Methods for preparing e.g. homogenates and extracts, such as protein extracts, from cells or other samples are well known in the art and can be readily adapted in order to obtain a sample that is compatible with the methods of the invention.

The term "contacting" as used herein, refers generally to providing access of one component, reagent, analyte or sample to another. For example, contacting can involve mixing a solution comprising a binding pair with a sample comprising an analyte. The solution comprising one component, reagent, analyte or sample may also comprise another component or reagent, such as dimethyl sulfoxide (DMSO) or a detergent, which facilitates mixing, interaction, uptake, or other physical or chemical phenomenon advantageous to the contact between components, reagents, analytes and/or samples. In one embodiment of the invention, contacting involves adding a solution comprising a binding pair to a sample comprising an analyte utilizing a delivery apparatus, such as a pipette-based device or syringe-based device.

The term "detecting" as used herein refers to any method of verifying the presence of a given molecule. The techniques used to accomplish this may include, but are not limited to, PCR, nucleotide sequencing, PCR sequencing, molecular beacon technology, hybridization, hybridization followed by PCR, fluorescence, radiolabelling, phosphorescence and absorbance. Examples of reagents that may be used for detection include, but are not limited to, radiolabels, enzymatic labels (e.g. horseradish peroxidase, alkaline phosphatase), fluorescence, phosphorescence, bioluminescence, chemiluminescence, affinity labels (e.g. biotin, avidin, or streptavidin) and other reagents well known by those of skill in the art.

As used herein, the term "distinguishable" refers to an ability to distinguish experimentally between different markers, species or analytes. In certain embodiments of the invention, a binding pair or assay of the present invention may be used to detect multiple analytes. In certain of these embodiments, none of the nucleic acid markers will consist of sequences identical in both length and sequence. Two markers may comprise the same core sequence, but the markers will be distinguishable on the basis of size and/or different sequences. In preferred embodiments, the detection products will be different in length. In other embodiments, the markers will have sequences which bind to different sequence-specific probes. These embodiments are not limiting, and other embodiments can be envisioned being used with the invention.

The terms "polynucleotide" and "nucleic acid (molecule)" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-stranded, double-stranded and triple helical molecules. "Oligonucleotide" refers generally to polynucleotides of between 5 and about 100 nucleotides of single- or double-stranded nucleic acid, typically DNA. Oligonucleotides are also known as oligomers or oligos and may be isolated from genes, or synthesized (e.g., chemically or enzymatically) by methods known in the art. A "primer" refers to an oligonucleotide, usually single-stranded, that provides a 3'-hydroxyl end for the initiation of enzyme-mediated nucleic acid synthesis. The following are non-limiting embodiments of polynucleotides: a gene, a gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine.

Sugar modifications (e.g., 2'-o-methyl, 2-fluor and the like) and phosphate backbone modifications (e.g., morpholino, PNA', thioates, dithioates and the like) can be incorporated singly, or in combination, into the nucleic acid molecules of the present invention. In one embodiment, for example, a nucleic acid of the invention may comprises a modified sugar and a modified phosphate backbone. In another embodiment, a nucleic acid of the invention may comprise modifications to sugar, base and phosphate backbone.

The term "nucleic acid marker" refers to a nucleic acid molecule that will produce a detection product of a predicted size or other selected characteristic when used with appropriately designed oligonucleotide primers in a nucleic acid amplification reaction, such as a PCR reaction. Skilled artisans will be familiar with the design of suitable oligonucleotide primers for PCR and programs are available commercially and over the Internet to facilitate this aspect of the invention (see, for example, the http site: bibiserv.techfak.unibielefeld.de/genefisher). A nucleic acid marker may be linear or circular. In preferred embodiments, the nucleic acid marker will comprise a predetermined, linear nucleic acid sequence with binding sites for selected primers located at or near each end. In a circular DNA nucleic acid molecule, the primers will be internal rather than at an end, and a single primer may be used, e.g. for Rolling Circle Amplification. Amplified DNA may be detected using any available method, including, but not limited to techniques such as real-time PCR, SYBR® Green staining, or ethidium bromide staining. In other embodiments of the invention, the binding sites for the amplification primers flank an undefined DNA sequence of defined length, or a DNA sequence that comprises another identifiable characteristic, such as a detectable sequence, in addition to undefined sequences. In some embodiments, the nucleic acid marker is distinguished by the size or mass of the amplified sequences; thus, the DNA sequence between the primers need not be defined as to the exact sequence, just as to the number of bases. Alternatively, the size and/or sequence of the entire nucleic acid marker need not be defined as long as a binding site for a molecular beacon (see, infra) is supplied. In further embodiments, the DNA sequence located between the primer binding sites comprises a "characteristic identification sequence" capable of being detected during the PCR reaction. Fluorescent signal generation may, for example, be sequence-specific (Molecular Beacons, TaqMan®, fluorogenic primers, such as the LUX™ primers (Invitrogen (Carlsbad, Calif.)) or mass dependent (e.g., SYBR® Green, Ethidium Bromide). The examples provided are not meant to be an exhaustive list of possible nucleic acid detection schemes as those skilled in the art will be aware of alternative markers suitable for use in the methods of the present invention.

The term "specificity molecule" as used herein refers to any molecule that is capable of specifically binding another molecule. In one embodiment, the specificity molecule is an antibody. In other embodiments of the invention, specificity molecules can include, without limitation: biological receptor molecules, such as the insulin receptor; ligands for receptors, (e.g., insulin for the insulin receptor); antigens (e.g., to bind to antibodies) and biological, chemical or other molecules that have affinity for another molecule, such as biotin and avidin. The specificity molecules of the present invention need not comprise an entire naturally occurring molecule but may consist of only a portion, fragment or subunit of a naturally occurring molecule, as for example the Fab fragment of an antibody. Specificity molecules may be generated by any method known in the art. For example, antibodies may be found in an antiserum, prepared from a hybridoma tissue culture supernatant or ascites fluid, or may be derived from a recombinant expression system, as will be well known in the art. Fragments, portions or subunits of e.g., an antibody, receptor or other species, may be generated by chemical, enzymatic or other means, yielding for example, well-known (e.g., Fab, Fab') or novel molecules. The present invention also contemplates that specificity molecules can include recombinant, chimeric and hybrid molecules, such as humanized and primatized antibodies, and other non-naturally occurring antibody forms. Those skilled in the art will recognized that the non-limiting examples given above describing various forms of antibodies can also be extended to other specificity molecules such that recombinant, chimeric, hybrid, and truncated forms of non-antibody molecules can be used in the methods of the present invention.

By the terms "specifically binding" and "specific binding" as used herein is meant that an antibody or other molecule, especially a specificity molecule of the invention, binds to a target such as an antigen, ligand or other analyte, with greater affinity than it binds to other molecules under the specified conditions of the present invention. Antibodies or antibody fragments, as known in the art, are polypeptide molecules that contain regions that can bind other molecules, such as antigens. In various embodiments of the invention, "specifically binding" may mean that an antibody or other specificity molecule binds to a target analyte molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. Whenever a range appears herein, as in "1-10 or one to ten, the range refers without limitation to each integer or unit of measure in the given range. Thus, by 1-10 it is meant each of 1, 2, 3, 4, 5, 6, 7, 8, 9, 10 and any subunit in between.

"Polyclonal Antibodies" or "PAbs," are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate, optionally supplemented with adjuvants. Polyclonal antibodies may be unpurified, purified or partially purified from other species in an antiserum. Techniques for the preparation and purification of polyclonal antibodies are well-known in the art and are described in various general and more specific references, including but not limited to Kabat & Mayer, Experimental Immunochemistry, 2d ed., (Thomas, Springfield, Ill. (1961)); Harlow & Lane, Antibodies: A Laboratory Manual (Cold Spring Harbor Laboratory Press, Cold Spring Harbor, N.Y. (1988)); and Weir, Handbook of Experimental Immunology, 5th ed. (Blackwell Science, Cambridge, Mass. (1996)).

"Monoclonal antibodies," or "MAbs," which are homogeneous populations of antibodies to a particular antigen, may be obtained by any technique that provides for the production of antibody molecules, such as by continuous culture of cell lines. These techniques include, but are not limited to the hybridoma technique of Köhler and Milstein, Nature, 256: 495-7 (1975); and U.S. Pat. No. 4,376,110), the human B-cell hybridoma technique (Kosbor, et al., Immunology Today, 4:72 (1983); Cote, et al., Proc. Natl. Acad. Sci. USA, 80:2026-30 (1983)), and the EBV-hybridoma technique (Cole, et al., in Monoclonal Antibodies And Cancer Therapy, Alan R. Liss, Inc., New York, pp. 77-96 (1985)). Such antibodies may be of any immunoglobulin class including IgG, IgM, IgE, IgA, IgD and any subclass thereof. The hybridoma producing the MAb of this invention may be cultivated in vitro or in vivo. Production of high titers of MAbs in vivo makes this a presently preferred method of production.

In addition, techniques developed for the production of "chimeric antibodies" (Morrison, et al., Proc. Natl. Acad. Sci., 81:6851-6855 (1984); Takeda, et al., Nature, 314:452-54 (1985)) by splicing the genes from a mouse antibody molecule of appropriate antigen specificity together with genes from a human antibody molecule of appropriate biological activity can be used. A chimeric antibody can be a molecule in which different portions are derived from different animal species, such as those having a variable region derived from a murine MAb and a human immunoglobulin constant region.

Alternatively, techniques described for the production of single chain antibodies (U.S. Pat. No. 4,946,778; Bird, Science 242:423-26 (1988); Huston, et al., Proc. Natl. Acad. Sci. USA, 85:5879-83 (1988); and Ward, et al., Nature, 334:544-46 (1989)) can be adapted to produce gene-single chain antibodies suitable for use in the present invention. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed (Huse, et al., Science, 246:1275-81 (1989)) to allow rapid and easy identification of monoclonal Fab fragments with the desired specificity.

The term "hapten" as used herein, refers to a small proteinaceous or non-protein antigenic determinant which is capable of being recognized by an antibody. Typically, haptens do not elicit antibody formation in an animal unless part of a larger species. For example, small peptide haptens are frequently coupled to a carrier protein, such as keyhole limpet hemocyanin, in order to generate an anti-hapten antibody response. "Antigens" are macromolecules capable of generating an antibody response in an animal and being recognized by the resulting antibody. Both antigens and haptens comprise at least one antigenic determinant or "epitope," which is the region of the antigen or hapten which binds to the antibody. Typically, the epitope on a hapten is the entire molecule.

The term "sandwich pair antibodies" or "sandwich antibody pairs," as used herein, refers to a pair of typically monospecific antibodies, e.g. monoclonal antibodies, that are suitable for use in a sandwich format immunoassay. Each antibody of the pair binds to a different epitope on the same molecule and both antibodies of the pair can bind to the antigen at the same time. Methods for identifying pairs of antibodies suitable for sandwich assays will be well known to those in the art. The skilled artisan will also recognize that various other molecules can be used as sandwich pairs. For example, a receptor analyte can be sandwiched between a ligand for that receptor and an antibody that binds to an epitope on the receptor that is not involved in ligand binding. Thus, an antibody and ligand can be used as a sandwich pair for a receptor analyte.

"Receptor" or "biological receptor" typically refers to a molecular structure within or on the surface a cell characterized by selective binding of a specific substance (e.g. a "ligand") and resulting in a specific physiologic effect that accompanies the binding. Examples of receptors include cell surface receptors for peptide hormones, neurotransmitters, antigens, complement fragments, immunoglobulins and cytoplasmic receptors for steroid hormones. As used herein, however, the receptor will typically be isolated and purified and need not effect or be capable of effecting a physiological or other biological effect. The methods of the present invention exploit the selective binding of the receptor to the specific substance.

The term "ligand" refers generally to a molecule that binds to a receptor. Typically, a ligand is a small, soluble molecule, such as a hormone or neurotransmitter.

The term "solid support" refers to any solid phase that can be used to immobilize e.g., an analyte, an antibody or a complex. Suitable solid supports will be well known in the art and include the walls of wells of a reaction tray, such as a microtiter plate, the walls of test tubes, polystyrene beads, paramagnetic or non-magnetic beads, nitrocellulose membranes, nylon membranes, microparticles such as latex particles, and sheep (or other animal) red blood cells. Typical materials for solid supports include, but are not limited to, polyvinyl chloride (PVC), polystyrene, cellulose, nylon, latex and derivatives thereof. Further, the solid support may be coated, derivatized or otherwise modified to promote adhesion of the desired molecules (e.g., analytes) and/or to deter non-specific binding or other undesired interactions. The choice of a specific "solid phase" is usually not critical and can be selected by one skilled in the art depending on the assay employed. Thus, latex particles, microparticles, paramagnetic or non-magnetic beads, membranes, plastic tubes, walls of microtiter wells, glass or silicon chips, and red blood cells are all suitable sold supports. Conveniently, the solid support can be selected to accommodate various detection methods. For example, 96 or 384 well plates can be used for assays that will be automated, for example by robotic workstations, and/or those that will be detected using, for example, a plate reader. For methods of the present invention that may involve an autoradiographic or chemiluminescent detection step utilizing a film-based visualization, the solid support may be a thin membrane, such as a nitrocellulose or nylon membrane. According to one embodiment of the invention in which sandwich immunoassays are performed, the walls of the wells of a reaction tray are typically employed. In alternative embodiments of the instant invention, paramagnetic beads may be used as a solid support. Suitable methods for immobilizing molecules on solid phases include ionic, hydrophobic, covalent interactions and the like, and combinations thereof. However, the method of immobilization is not typically important, and may involve uncharacterized adsorption mechanisms. A solid support as used herein, may thus refer to any material that is insoluble, or can be made insoluble by a subsequent reaction. The solid support can be chosen for its intrinsic ability to attract and immobilize a capture reagent. Alternatively, the solid phase can retain an additional receptor that has the ability to attract and immobilize a capture reagent. The additional receptor may include a substance that is oppositely charged with respect to either the capture reagent itself or to a charged substance conjugated to the capture reagent. In yet another embodiment of the invention, an additional receptor molecule can be any specific binding member that is immobilized upon (attached to) the solid phase and which has the ability to immobilize a capture reagent through a specific binding reaction. The additional receptor molecule enables indirect immobilization of the capture reagent to a solid phase before or during the performance of the assay. The solid phase thus can be a plastic, derivatized plastic, paramagnetic or non-magnetic metal, glass or silicon surface of a test tube, microtiter well, sheet, bead, microparticle, chip, or other configurations known to those of ordinary skill in the art.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. Polypeptides usually comprise at least about 100 to 1000 amino acids in length, more typically at least about 150 to 600 amino acids, and frequently at least about 200 to about 500 amino acids. "Proteins" include single polypeptides as well as complexes of multiple polypeptide chains, which may be the same or different. Multiple chains in a protein may be characterized by secondary, tertiary and quaternary structure as well as the primary amino acid sequence structure; may be held together, for example, by disulfide bonds; and may include post-synthetic modifications such as, without limitation, glycosylation, phosphorylation, truncations or other processing. Antibodies such as IgG proteins, for example, are typically comprised of four polypeptide chains (i.e., two heavy and two light chains) that are held together by disulfide bonds. Furthermore, proteins may include additional components such associated metals (e.g., iron, copper and sulfur), or other moieties. The definitions of peptides, polypeptides and proteins include, without limitation, biologically active and inactive forms; denatured and native forms; as well as variant, modified, truncated, hybrid, and chimeric forms thereof. The peptides, polypeptides and proteins of the present invention may be derived from any source or by any method, including, but not limited to extraction from naturally occurring tissues or other materials; recombinant production in host organisms such as bacteria, fungi, plant, insect or animal cells; and chemical synthesis using methods that will be well known to the skilled artisan.

The term "conjugate" as used herein refers to two molecules that have been covalently attached or otherwise linked together. In one embodiment, a nucleic acid conjugate is generated by covalently linking a nucleic acid to a protein, polypeptide or other specificity molecule. In a preferred embodiment of the invention, the protein, polypeptide or other specificity molecule is covalently attached to a nucleic acid via a linking group to form a conjugate.

A "kit" for detecting the presence of an analyte in a sample by the methods of the invention may, by way of example, comprise at least one container means having disposed therein a binding pair specific for the selected analyte. The kit may further comprise other container means comprising one or more of the following: buffers, solutions or other reagents and materials necessary for performing analyte detection; reagents capable of amplifying the nucleic acid probe components of the binding pairs; and reagents capable of detecting the presence of nucleic acid components following amplification. Preferably, the kit further comprises instructions for use. The kit, if intended for diagnostic use, may also include notification of a FDA approved use and instructions therefor.

Specifically, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers may include a container which will accept a test sample, a container which contains the probe or primers used in the assay, containers which contain buffers and reagents (such as phosphate buffered saline, Tris-buffers, and the like), and containers which contain the reagents used to detect the marker nucleic acid, amplified product, or the like. One skilled in the art will readily recognize that preformed binding pairs and/or materials, supplies and reagents necessary to prepare binding pairs can readily be incorporated into one of the established kit formats that are well known in the art.

A kit for coupling DNA to an antibody or other specificity molecule by the methods of the invention may comprise at least one container means having disposed therein lyophilized, activated DNA. The kit may further comprise other containers comprising one or more of the following: reagents, buffers and agents capable of detecting the presence of nucleic acid after the reaction. Preferably, the kit further comprises instructions for use. One skilled in the art will readily recognize that the activated nucleic acids described in the present invention can readily be incorporated into one of the established kit formats that are well known in the art.

Homogeneous Analyte Detection Assay

The present invention generally provides compositions, methods and kits for the use of novel nucleic acid labeled-binding pairs of defined and limited stability under defined conditions for the detection of analytes, particularly homogenous sensitive analyte detection.

Binding Pairs

In one embodiment, the invention provides binding pairs that are useful for detecting analytes. Binding pairs of the present invention are formed between two binding members, each having a specificity molecule coupled to a nucleic acid, as shown in FIG. 1. The nucleic acid component of the binding members are complementary over at least a part of their length, and can form a duplex through which the two members of the binding pair are joined (see FIG. 1).

Specificity Molecule Components of Binding Pairs

The specificity molecules of each binding pair direct the interaction of the pair to a desired analyte. A specificity molecule of the invention, as described supra, can be any molecule that is capable of interacting with another molecule, such as an analyte. In a preferred embodiment, specificity molecules interact with an analyte with high specificity and affinity.

In one aspect of the invention, the specificity molecule is a receptor. In another aspect, the specificity molecule is a ligand. In yet another aspect of the invention, the specificity molecule is an antibody.

The individual specificity molecules of a binding pair can both be the same type of molecule or can be different types of molecules. In one embodiment, both specificity molecules in a pair are receptors. In another embodiment, both specificity molecules in pair are ligands. In another, both are antibodies. In still another, both are antigens. In yet another embodiment, one specificity molecule is a ligand and the other specificity molecule is a receptor. In still another embodiment, one or both of the specificity molecules in a binding pair is a nucleic acid. In one aspect of this embodiment, the target analyte is a complementary nucleic acid. In another aspect of this embodiment, the target analyte is a DNA, an RNA or a protein, or a component of a complex thereof. In still another aspect of this embodiment, the target analyte is a complex comprising a nucleic acid and a protein and one of the specificity molecules of the binding pair is a nucleic acid that is complementary to the nucleic acid component of the target analyte and the other specificity molecule of the binding pair is a protein (i.e., an antibody, antigen, ligand, receptor, etc.) that binds specifically to the protein component of the target analyte. In a preferred embodiment, at least one specificity molecule of a binding pair is an antibody.

Antibodies are particularly useful as specificity molecules. All types of antibodies described supra are useful for imparting specificity to a binding pair, including but not limited to monoclonal antibodies, polyclonal antibodies, chimeric antibodies, hybrid antibodies, recombinant antibodies, humanized antibodies, primatized antibodies, truncated antibodies, single chain antibodies and the like.

When two antibodies are used to form a binding pair, the two antibodies may have the same or different specificities. In one embodiment of the invention, the two antibodies recognize the same epitope and that epitope is present multiple times on a single analyte. For example, both antibodies in a binding pair may recognize a receptor that is present in multiple copies on the surface of a cell analyte. In another embodiment, the antibodies recognize different epitopes on a single analyte molecule. In certain aspects of this embodiment, both antibodies can bind simultaneously to a single analyte molecule. The so called "sandwich pair" antibodies of this aspect of the invention will be well known to those skilled in the art.

Nucleic Acid Components of Binding Pairs

Each specificity molecule in a binding pair is coupled to or "labeled" with a nucleic acid molecule (i.e., a nucleic acid marker). According to one aspect of the invention, the nucleic acids are single-stranded. In another aspect, the nucleic acids are partially single-stranded. In yet another embodiment, the nucleic acid is all DNA, all RNA or a mixture of DNA and RNA. In other embodiments, nucleotide analogs or derivatives may be used. In another embodiment PNA is used as part or all of the nucleic acid. The specificity molecule may be coupled to either the 3' or 5' end of the nucleic acid. In one embodiment of the invention, the terminal free ends of the two nucleic acids in a binding pair are complementary such that they can hybridize to form a duplex nucleic acid region of limited and defined stability. In one aspect of this embodiment, the terminal free ends that form a duplex are the 3' ends of the nucleic acids. In another embodiment, the terminal free end of one of the nucleic acids of a binding pair is complementary to a sequence of the other nucleic acid of that binding pair at a point other than the terminal end of one of the nucleic acid. In one aspect of the invention, the 3' end of the first nucleic acid forms a duplex with an internal sequence of the second nucleic acid. In certain embodiments, the nucleic acid is coupled to a specificity molecule via one or more linkers or spacers.

The nucleotide sequence of the nucleic acids of the present invention is of less importance than the functional roles they are required to perform. Accordingly, the sequence of the nucleic acids, as well as the length of the nucleic acid component of the binding pair, may vary considerably, provided the nucleic acid component of the binding pair can still perform the functional roles they are required to perform. Importantly, the sequence and length of the nucleic acids of the binding pair are not limited to those exact sequences and lengths of the exemplary binding pairs disclosed herein. The nucleic acids of the binding pair thus can be of different lengths and or sequence. An important function of the nucleic acid component of the binding pairs of the present invention is to provide a highly sensitive label for analyte detection. In one embodiment, the nucleic acid is amplified and detected as a measure of analyte concentration. The nucleic acid can be amplified using well established methods. Exemplary amplification methods include those described in various U.S. patents, the contents of which are incorporated by reference herein in their entirety: PCR (see e.g. U.S. Pat. No. 4,683, 202), TMA (see e.g. U.S. Pat. No. 5,399,491); SDA (see e.g. U.S. Pat. No. 5,270,184), and LCR (see e.g. U.S. Pat. No. 5,427,930).

A wide variety of nucleotide sequences can be used for amplification. Similarly, the length of the nucleic acid can be varied considerably. In one embodiment, the nucleic acids of the invention are designed to avoid intramolecular hairpin formation in order to increase the efficiency with which they can be amplified. In certain aspects of the invention, the nucleic acid is detected using a nonspecific intercalating fluorescent dye, such as SYBR® Green. According to this embodiment, the strength of the detection signal will be a function of the length of the nucleic acid detected.

It is well known that the stability of a nucleic acid duplex is dependent in part on the length of the region of complementarity between the nucleic acid strands in the duplex. A longer complementarity region or "overlap" between nucleic acids increases the stability of the duplex that is formed. Conversely, a shorter overlap leads to a less stable duplex. Nucleic acids of the present invention are designed to have defined stability that can be manipulated by altering length, temperature, solvent and other conditions. Factors that influence the stability of the hybrid include, but are not limited to, the concentration of the nucleic acid-labeled binding pairs, salt concentration, temperature, organic solvents such as ethanol, DMSO, tetramethylammonium ions (TMA$^+$), base pair mismatches and the like.

In one aspect of the invention, the nucleic acids are designed to form intra-binding pair duplexes. In another aspect of the invention, the nucleic acid duplexes of a binding pair can be dissociated under defined conditions and thus have limited stability under certain conditions.

In one embodiment of the invention, reaction conditions are designed to maximize duplex formation between the members of binding pairs bound to their respective target analytes while minimizing duplex formation between members of binding pairs that are not bound to target analytes. In another embodiment, the duplexes remain stable during binding to an analyte, but can be selectively dissociated or melted by an assay operator.

Under these conditions, the thermodynamic conditions favors the unbound pairs to be unhybridized. In certain embodiments of the invention, less than about 1% of the binding pairs are not bound to analyte. In other embodiments, less than about 0.1%, 0.01%, or 0.001% of the binding pairs are not bound to analyte. In other embodiments, a competitor nucleic acid (e.g., complementary to a region of duplex formation between binding pair nucleic acids) may be used to prevent free binding members from re-associating. A similar effect may be obtained by designing one of the nucleic acids in a binding pair to form a small hairpin when it is not hybridized to the nucleic acid of its binding partner.

Once formed, the stability of the complex between the binding pair and the target analyte can be enhanced by using a polymerase enzyme to extend 3' ends of the nucleic acid duplex as described in U.S. Pat. No. 5,635,602, the contents of which are incorporated by reference herein in its entirety.

Nucleic acid markers of the present invention can be detected by incorporating any one of a number of labels into one or both of the binding pair nucleic acids. Examples of markers suitable for use in the present invention include intercalating fluorescent molecules such as SYBR® Green and ethidium bromide; FRET fluorescent resonance energy transfer pairs, such as fluorescein and rhodamine; radioactive compounds, bioluminescent compounds, chemiluminescent compounds such as acridinium ester; chemiluminescent quencher pairs; and reagents that hybridize to nucleic acid in a sequence-specific manner, such as Molecular Beacons (Kramer), TaqMan® and fluorogenic primers (e.g. LUX™ primers; Invitrogen, Carlsbad, Calif.). In addition fluorescent nucleic acid triphosphates (NTPs and dNTPs) can be incorporated during an extension of the 3' ends of the duplexed nucleic acid pairs. Furthermore, it is possible to incorporate the labels by nick translation and other means.

Nucleic Acid Binding Pair Analyte Assay

The present invention also provides methods for detecting analytes using binding pairs. In one embodiment, an analyte-specific binding pair, as described above, is contacted with its analyte, to form a complex. The members of the binding pair are joined by the intermolecular duplex of defined and limited stability formed between the two nucleic acids. Furthermore, the binding members are locked in place in close proximity, and therefore high local concentration, by virtue of their association with the analyte. The nucleic acid duplexes may then be dissociated and allowed to reassociate.

Any method known in the art may be used to dissociate the duplexes. In one embodiment of the invention, dissociation may be accomplished by heating the complexes above the melting temperature of the nucleic acid duplex. In another aspect of the invention, the salt concentration or ionic strength may be decreased. In yet another aspect of the invention, a chemical or biological agent may be added to the complex to dissociate the duplexes.

In another aspect of the invention, the reassociation of the nucleic acids of binding pair members not complexed with analyte may be prevented or eliminated by dilution. In another aspect, the dilution or other condition of the reaction does not allow substantial reassociation of excess free binding members. Generally, conditions which do not allow substantial reassociation involve less than 5%, typically less than 1%, frequently less than 0.1% and most often less than 0.01% reassociation of excess free binding members. According to this embodiment, binding pairs are contacted with an analyte such that a complex between the binding pair and the analyte is formed. The complexes are then diluted such that hybridization of proximity-bound nucleic acid markers is favored but hybridization in bulk solution is disfavored. Under these conditions, the extension of 3' ends of the marker nucleic acid occurs predominantly or exclusively in the complexed and hybridized marker nucleic acids, while the uncomplexed nucleic acids are not hybridized and therefore extension from 3' ends does not occur.

According to this method of the invention, the extended duplexes are then detected as a means for analyte detection. In one embodiment of the invention, a nucleic acid comprising the duplex is amplified to facilitate detection. Amplification may be accomplished by any method known in art. Suitable methods include, but are not limited to PCR, LCR, SDA, and TMA.

Typically, nucleic acid amplification methods rely on primed enzymatic synthesis of DNA. According to such methods, a primer with a free 3' OH is hybridized to a single-strand DNA or RNA template. The 3' OH can then form the initiation point for extension using a polymerase, examples of which are well known in the art and include, without limitation, Taq DNA polymerase, DNA Polymerase I, Klenow Fragment of DNA Polymerase, T4 DNA polymerase, T7 DNA Polymerase, Reverse Transcriptase, phi29 DNA Polymerase, Bst DNA Polymerase, AccuPrime™ (Invitrogen), Pfx DNA Polymerase (Invitrogen), FideliTaq™ DNA Polymerase (Amersham Biosciences), Sequenase™, Thermo Sequenase™ DNA, Hot Tub™ DNA Polymerase (Amersham Biosciences), Vent® Polymerase (New England Biolabs), and 9° N$_m$ DNA Polymerase.

In one aspect of the invention, the template for PCR is a nucleic acid molecule comprising the duplex region of the two strands of nucleic acid complexed to the analyte via their respective specificity molecules. As will be understood by those skilled in the art, a template for PCR may be longer than the desired PCR product. The two individual PCR primers may hybridize internally and initiate DNA synthesis, each at a particular site on one strand of the nucleic acid template. The resulting PCR product typically has a 5' terminus defined by one primer and a 3' terminus defined by the other primer.

The amplification products can then be detected, for example by staining with ethidium bromide, silver staining, autoradiography, dot blotting, slot blotting, or southern blotting. Alternatively, detection can be accomplished by incorporating a detection molecule into one or both of the nucleic acids, the amplification product or the duplex region of the complex. Detection molecules suitable for use in the methods of the present invention include, but are not limited to fluorescent molecules, fluorescence quencher molecules, chemiluminescent compound, chemiluminescence quencher molecules, a fluorescent nucleotides, enzymatic labels, and radiolabels.

In certain embodiments of the invention, duplex detection may be facilitated by incorporating an acridinium ester into the duplex region of the complex and selectively hydrolyzing the label in first and second binding pair members that have not formed a nucleic acid duplex.

3' Extension from Duplexes and Generation of Primer Binding Sites

The present invention provides methods for detecting analytes through the amplification of binding pair nucleic acid duplexes in which one or both primer binding sites are absent from nucleic acid marker sequences. According to this embodiment, one or more primer binding sites are generated after the binding pair has bound an analyte. For example, one or both of the nucleic acid marker sequences may incorporate a sequence identical to the desired primer sequence, outside of the duplex region. In other words, the primer binding sites for amplification are not present in the binding pair nucleic acids but are only formed after the 3' ends of nucleic acid duplexes are extended.

Figure 2:
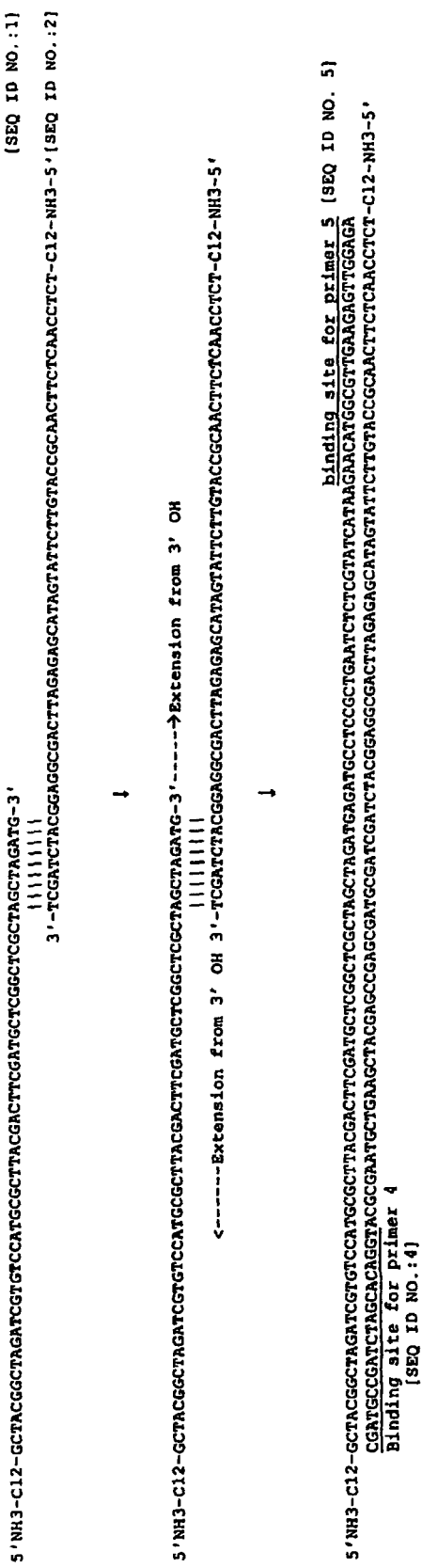
FIG. 2 provides a general scheme for duplex formation, 3' extension and PCR amplification of a nucleic acid pair comprising SEQ ID NO.:1 and SEQ ID NO.:2.

In this embodiment, no region complementary to the primer (i.e., no primer site) is present in the marker nucleic acid. Following hybridization, however, the 3' end of one or both of the markers may be extended using a suitable polymerase. The extension encompasses the sequence identical to the desired primer sequence, thereby generating a complementary primer binding site which may be used in subsequent amplification steps for binding to the primer (FIGS. 2 and 3). In one aspect of this embodiment, the amplification primer will neither hybridize nor initiate nucleic acid synthesis/amplification unless a duplex region is formed between the first and second nucleic acid markers and subsequently extended. In another aspect of the invention, the background non-specific detection is reduced because only hybridized molecules are detected.

Oligonucleotides 60 bases long having a 5' amino $C_{12}$ spacer arm (Spacer $C_{12}$ CE Phosphoramidite; 12-(4,4'-Dimethoxytrityloxy)dodecyl-1-[(2-cyanoethyl)-(N,N-diisopropyl)]-phosphoramidite) with the following nucleotide sequences have been found suitable for use in this aspect of the of the present invention:

```
                                           [SEQ ID NO.: 1]
(1) 5' NH3-C12-GCTACGGCTAGATCGTGTCCATGCGCTTACGACTT
CGATGCTCGGCTCGCTAGCTAGATG 3'

[SEQ ID NO.: 2]
(2) 5' NH3-C12-TCTCCAACTCTTCAACGCCATGTTCTTATGATACG
AGAGATTCAGCGGAGGCATCTAGCT 3'

[SEQ ID NO.: 3]
(3) 5' NH3-C12-TCTCCAACTCTTCAACGCCATGTTCTTATGATACG
AGAGATTCATCATCTAGCTAGCGAG-3'
```

Oligonucleotide (1) [SEQ ID NO.:1] is complimentary to both oligonucleotide (2) [SEQ ID NO.:2] and oligonucleotide (3) [SEQ ID NO.:3] for the last 9 and 15 bases, respectively, at the 3' ends. The length of the duplex formed between the oligos has a specific Gibbs Free Energy ($\Delta G$), which is controlled by nearest neighbor base sequence. See Breslauer, et al., *Proc. Nat'l. Acad. Sci. U.S.A.* 83: 3746-3750 (1986). The 9 and 15 base-pair overlaps have melting temperatures ($T_m$'s) of 26° C. and 42° C., respectively, in 50 mM NaCl according to the formula:

$$T_m = 64.9 + 41*(yG+zC-16.4)/(wA+xT+yG+zC)$$

where w, x, y, z are the number of the bases A, T, G, C in the sequence, respectively. See e.g., http://www.basic.nwu.edu/biotools/oligocalc.html. The overlapping strands hybridize (>50% duplex) when present in solution at concentrations greater than 50 nM at 25° C., 50 mM NaCl. The strands exist predominately as monomers (<50% hybrid) at concentrations less than 100 pM at equilibrium. According to the principles of thermodynamics, complementary DNA strands such as these may transition between single- and double-stranded forms as a function of temperature, DNA concentration and salt effects. When hybridized, the 3' end of each strand can serve as the initiation point for synthesis of nucleic acid complementary to the other strand. Each strand may be extended in the presence of an appropriate DNA polymerase and nucleotide triphosphates, resulting in a 111 (FIG. 2) or 105 (FIG. 3) base pair DNA duplex. The newly formed duplex contains sequences that were not present initially in the partially overlapped structure. These new sequences can be replicated exponentially by PCR in the presence of the following downstream primers:

```
5' GCTACGGCTAGATCGTGTCCA 3'          [SEQ ID NO.: 4]
and

5' TCTCCAACTCTTCAACGCCATGTTC 3'      [SEQ ID NO.: 5]
```

Individual strands cannot replicate in the presence of these primers without forming the first chain extension product.

Figure 4:
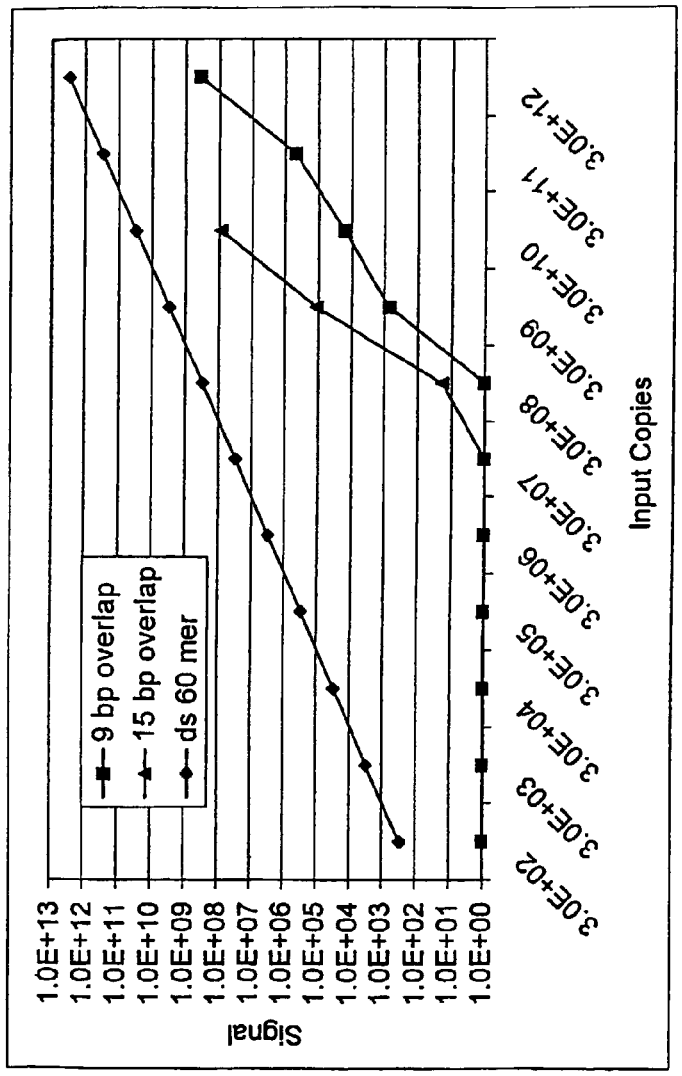
FIG. 4 shows the real-time PCR amplification (hot start) of both the 9 and 15 base pair overlapping oligonucleotide strands.

FIG. 4 shows the real-time PCR amplification (hot start) of both the 9 and 15 base pair overlapping oligonucleotide strands. It can be seen from this Figure that amplification does not occur until a sufficient concentration of strands are present to ensure the probability that one strand will be close enough to a complementary strand for hybridization and first chain extension. Increasing the concentration of overlapping strands results in an exponential increase in template generation, as measured by real-time PCR threshold cycle. Conversely, diluting this concentration, by washing a support for instance, exponentially decreases signal. Amplification of a normal 60-mer template is shown for comparison.

Proximity Effects in Binding Pair-Analyte Complexes

Figure 5:
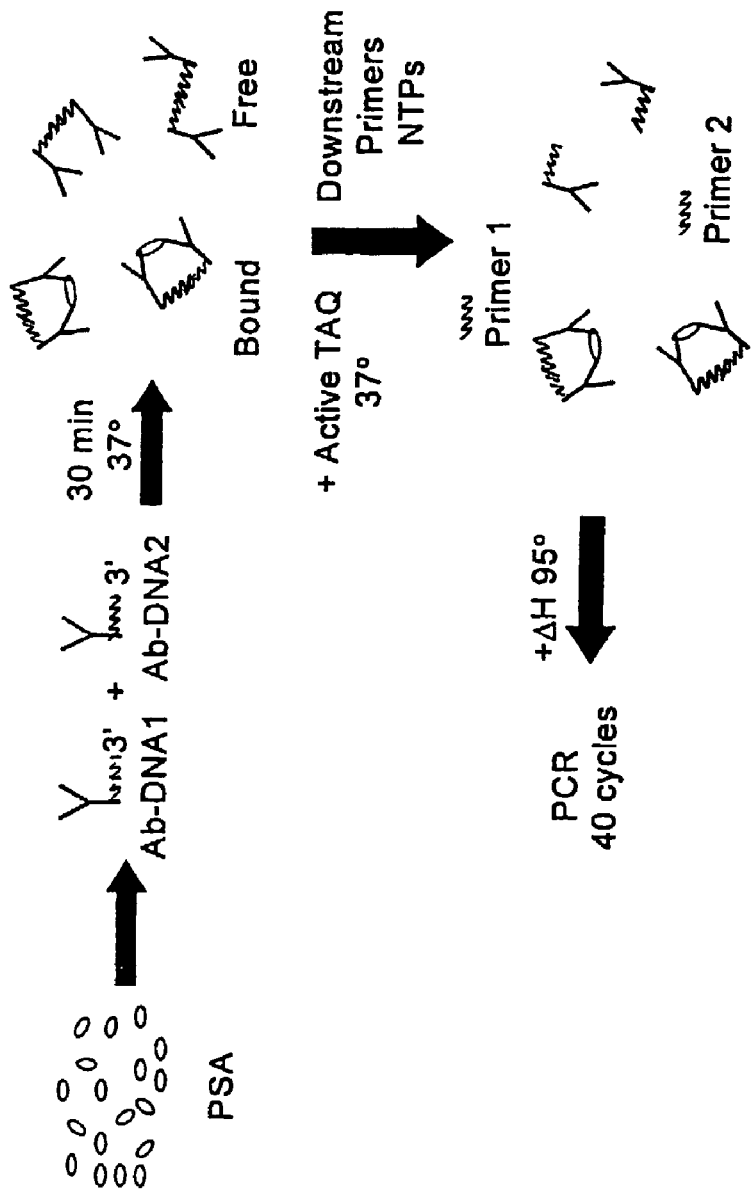
FIG. 5 shows a schematic representation of a homogeneous NADIA™.

Sandwich immunoassays employing overlapping oligonucleotide labels have been termed NADIA™ (Nucleic Acid Detection ImmunoAssay). Both homogenous and heterogeneous formats of NADIA have been demonstrated. A schematic representation of a homogeneous NADIA is given in FIG. 5.

Antibody binding members labeled with overlapping oligonucleotides also exhibit the PCR amplification effect shown in FIG. 4. Binding such DNA-Ab conjugates to the same antigen, or to an antigen coated surface, fixes the overlapping oligonucleotide strands in proximity to one another. This effectively increases the relative concentrations of both strands and the probability of template formation. The template, once formed, exhibits a linear relationship between concentration and real-time PCR threshold signal.

This proximity effect has implications for greatly reducing background signal arising from the nonspecific binding of template DNA-Ab conjugate when a capturing support is used (i.e. in a heterogeneous assay). The individual overlapping oligonucleotide sequences are not template molecules for amplification and, unlike DNA-Ab conjugates previously described, cannot be amplified by themselves with the selected primer set. Although the overlapping conjugates still bind nonspecifically, the binding is random. Random nonspecific binding of a relatively small number of copies of conjugate greatly diminishes the opportunity for proximal interaction and first chain extension.

The proximity effect may also be the basis for homogeneous sandwich assay formats of the present invention, in which a capturing solid support is unnecessary. According to a method of the present invention, conditions must be used which favor the hybridization and first chain extension of proximally bound overlapping conjugates and disfavor hybridization in the bulk solution. Any nonspecific hybridization of the conjugate pair in solution will elicit signal, as shown in FIG. 4. One embodiment of the present invention, therefore, entails employing the lowest conjugate concentration possible to maintain an acceptable immune complex formation rate. Adjustment of overlap length, salt conditions and temperature effects are also available to minimize random hybridization of the overlap sequences in the bulk solution.

Immunodetection of Cellular Analytes

Affinity purified polyclonal antibodies to *E. coli* 0157 have been conjugated to the overlapping oligonucleotide strands in order to demonstrate a heterogeneous NADIA format for the detection of intact microorganisms. Antibody attached to magnetic particles (Dynal, Lake Success, N.Y.) has been used to isolate and enrich *E. coli* 0157 cells from water samples and meat homogenate. The cell surface is estimated to exhibit several thousand copies of the specific antigen that was detected. Calculations show that the distance between randomly distributed sites fall within the spanning distance of overlapping oligonucleotides conjugated to anti-*E. coli* 0157. In this case, proximity binding is due to individual antigen spacing, as opposed to separate epitopes on a single protein antigen.

According to methods of the present invention (described below under Examples), polyclonal anti-*E. coli* 0157 (KPL, Gaithersburg, Md.) was labeled in three separate reactions with sequences (1) (2) and (3) and maintained as individual conjugates. *E. coli* 0157:H7 was obtained from ATCC (700728) and grown at 37° C. Cells from liquid culture were diluted in fresh media and incubated with 10 nM overlapping oligonucleotide-Ab conjugates for 1 hour at room temperature. The resulting cell-antibody complex was washed free of excess, unbound conjugate by centrifugation and resuspension in cold tris-buffered saline, effectively diluting the overlapping antibody reagent to below 1.0 pM. The washed cells were simultaneously streaked onto plates and assayed by incubation in PCR reagent mixture for 10 min at 33° C., followed by 40 cycles of real-time PCR in the presence of downstream primers. The presence of 10-50 cells, as determined by colony formation in overnight culture at 37° C., was sufficient to elicit signal above background in 2-3 hour assay, without culture.

Homogeneous Assays for Cellular Analytes

The present invention provides a method for detecting intact cells or viruses by forming a complex on the cell surface with a binding pair reagent. The binding pair reagent used for detecting intact cells, such as bacterial cells, is similar to that used for detecting a protein analyte that has two binding sites for two or more MAbs. In this case, the binding sites may comprise the same protein embedded in the cell surface. The binding pair reagent spans the distance between individual protein units.

The cells that may be detected according to this method include bacterial, animal, plant, insect and fungal cells. In one embodiment, the animal cell is a human cell, which may be diseased or healthy. For example, the method may be used to detect circulating cancer cells by employing binding pair comprising antibodies to cell surface tumor antigens.

Analyte Detection Using Binding Pairs Having 3'-5' Conjugation of Overlap DNA Markers Greatly enhanced assay sensitivity can be achieved by the use of binding pair reagents comprising one binding pair member (5' conjugate) comprising a first nucleic acid of an overlapping pair conjugated to the first specificity molecule (e.g. first MAb of a sandwich pair) at the 5' end and the other binding pair member (3'conjugate) comprising the complementary second nucleic acid strand of an overlapping pair conjugated to a second specificity molecule (e.g. second Mab) via the 3' end as illustrated in FIG. 6. According to this method, the 3' end of the 5' conjugate hybridizes to an internal sequence of the 3' conjugate, producing a binding pair where extension of the 3' end is directed away from the center of mass of the formed complex and towards a freely rotating terminus (the 5' end of the 3' complex). This orientation improves the efficiency of chain extension when compared to 3'-3' overlap binding pairs thereby allowing for greater steric access of polymerase and the dissipation of torsional stress during initial polymerization.

Homogeneous Assay Employing Enzymatic Digestion

Improved sensitivity for the homogeneous detection of analytes can be achieved by using binding members comprising specificity molecules, such as antibodies, conjugated to single-strand nucleic acids that have deoxyribose bases at the 5' end and ribose bases at the 3' end. According to this method, the DNA/RNA labels are complementary on the 3' ends for the entire stretch of RNA sequence and for short stretch of DNA sequence. In certain embodiments, the RNA sequence is at least about 20 bases long. In other embodiments the RNA sequence is at least about 30, 40, 50 or 60 bases long. According to one aspect of the invention, the RNA sequence is 26 bases long. The DNA-DNA duplex region is short, typically comprising less than 15 base pairs, frequently less than about 12 base pairs, and preferably less than about 10 base pairs in length. In various aspects of the invention, the DNA-DNA duplex is 12, 11, 10, 9, 8 or 7 base pairs in length.

According to this method, a nucleic acid duplex region of the analyte-binding pair complex, particularly the DNA/RNA heteroduplex regions, is stable at elevated temperatures, thereby ensuring the formation of a complex containing binding members locked into a specific orientation and distance from each other in the binding pair complex. Following complex formation, the RNA component of both the complexed and excess binding pair can be digested by the addition of RNase, leaving a short, relatively unstable binding pair joined by the residual DNA/DNA duplex. In one embodiment, the RNase is RNase H. Following RNase treatment, the unstable binding pair dissociates into its respective binding members upon raising the temperature. Only the binding members fixed into position on the complex rapidly reassociate upon reducing the temperature. The dissociated binding members that are not held in close proximity by the analyte cannot reform into a binding pair due to low concentration and limited stability of a short DNA/DNA duplex. In one aspect of this method, binding members with nucleic acid components of shortened 3' DNA overlap reduces the requirement for dilution of the complex formation reaction and, therefore, improves sensitivity further.

Nucleic acid strands comprising both deoxyribose and ribose nucleotide monomer, and having a 5' amino function may be synthesized by standard phosphoramidite chemistry. Alternatively, a short 3' DNA/DNA overlap may be filled in enzymatically with RNA polymerase.

Sensitive Homogeneous Assay for Analytes

By combining the features described above, a homogeneous assay has been devised for analytes such as protein antigens and microorganism that approaches the sensitivity achieved for nucleic acid detection. According to this method of the invention, a first specificity molecule (e.g. a first MAb of a sandwich pair or a first portion of polyclonal antibody) is conjugated to the 5' end of a chimeric DNA/RNA oligonucleotide. In one aspect of this method, the RNA portion of the DNA/RNA oligo comprises 30 bases at the 3' end. Typically, a unique primer site is located at the 5' DNA terminus of the DNA/RNA oligo. The second specificity molecule (e.g., second MAb or a second portion of polyclonal antibody) is conjugated to the 3' end of a DNA oligonucleotide optionally synthesized with one or more 3' phosphoramidite spacers to increase overall length. In one aspect of this method, the DNA oligo is at least 60 bases long. Typically, a unique primer binding site is located at the 5' end of the DNA oligo. According to this method, the oligonucleotides form a duplex of relatively long RNA-DNA hybrid, typically 20-40 base pairs in length, followed by a short stretch of DNA-DNA hybrid, of approximately 7-15 base pairs. (FIG. 7).

Figure 7:
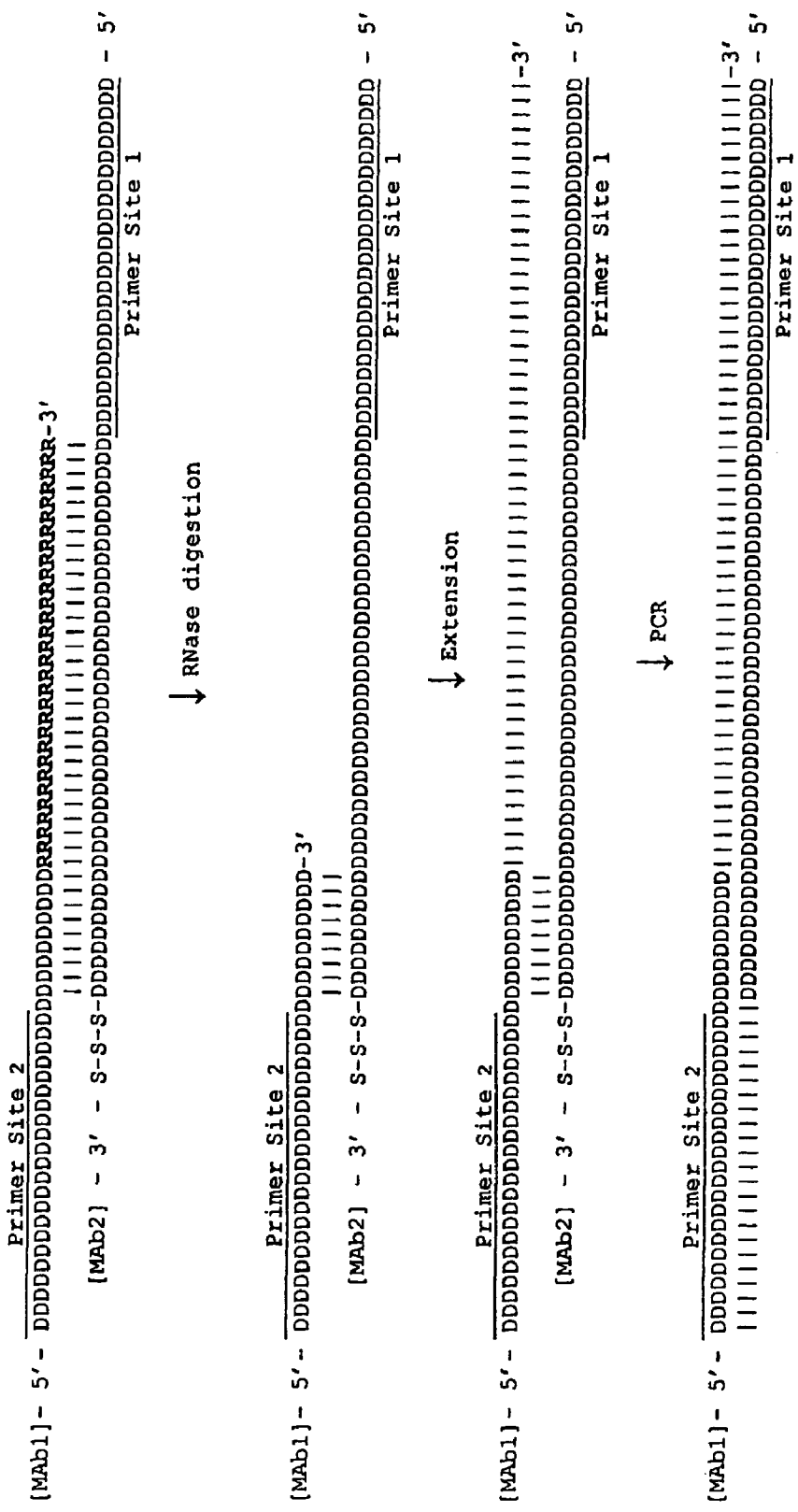
FIG. 7. illustrates the process for use of chimeric RNA/DNA oligonucleotides in analyte detection. "R" indicates the position of ribonucleotide bases, "D" indicates the position of deoxyribonucleotide bases and "S" indicates the position of spacer molecules.

After analyte complex formation, RNA digestion, melting and reannealing, the binding pairs of this embodiment can be extended by polymerase in only one direction from the exposed 3' DNA terminus (FIG. 7). Steric and torsional constraints imposed by 3' overlaps are eliminated, as described above. Enzymatic digestion of the binding pair results in a short, DNA-DNA duplex, which is relatively unstable and thereby minimizes reformation of binding pair from free binding members in the bulk solution.

It will be understood that the application of the teachings of the present invention to a specific problem or situation will be within the capabilities of one having ordinary skill in the art in light of the teachings contained herein. The invention will be further illustrated by reference to the following non-limiting Examples. The following examples, including experiments and results achieved, are provided for illustrative purposes only and are not to be construed as limiting the present invention.

EXAMPLES

Example 1

Activation of 5' Amino DNA Template

Two 60-base single-strand DNA sequences [SEQ ID NOS. 1 and 3] were synthesized to contain a single primary amine group attached to the 5' end via a 12-carbon spacer arm (Glen Research, Sterling, Va.). The sequences were complimentary to each other for the last 15 bases on the 3' terminus. Both were treated identically. The 5' amino-DNA (350 μg) was dissolved in 25 μl 0.05 M sodium phosphate buffer, pH 7.0. Disuccinimidyl suberate was dissolved in dry DMSO at a concentration of 10 mg/ml, and a 50 μl aliquot was added immediately to the DNA solution and mixed by gentle re-pipetting. After one minute at room temperature, the reaction mixture was injected onto a 0.5×20 cm G-25 (fine) column plumbed to a Pharmacia FPLC system. The column was equilibrated in 5 mM citric acid, adjusted to pH 5.4 with 0.1 M sodium hydroxide, and developed at a flow rate of 0.5 ml/min at room temperature. The first eluted peak was collected directly into an Microcon® YM-10 centrifugal ultra filtration (Millipore, Billerica, Mass.) unit embedded in ice. The suberate-activated template DNA was concentrated at 4° C. and 5000×g for 30 minutes, to 200-300 μl. The DNA concentration was quickly assessed by absorbance at 260 nm. Aliquots containing 1.0 $A_{260}$ unit (approximately 30 μl) were dispensed into micro centrifuge tubes containing 5 μl of 10% mannitol, and frozen immediately in dry ice/acetone bath. The frozen aliquots were lyophilized to dryness, sealed under dry argon and stored at −20° C.

The activity of the lyophilized, activated DNA was assessed by conjugation to a small amine-containing molecule. Glutathione at 50 mg/ml in 0.1 M sodium phosphate, pH 8.0 was reacted with a stoichiometric amount of N-ethyl maleimide (NEM). The pH was re-adjusted to 8.0 with sodium hydroxide. One $A_{260}$ unit of suberate-activated DNA was dissolved in 10 μl of NEM-treated glutathione, then diluted 25-fold with water to 4.0 $A_{260}$ units/ml. Conjugation with alkylated glutathione resulted in a slower migrating band compared to 5' amino DNA when electrophoresed on a 15% polyacrylamide TBE-urea gel. Suberate-activated DNA, purified and lyophilized under the conditions described above, typically exhibited nearly 100% conjugation to NEM-treated glutathione, indicating complete suberate activation and maintenance of amine reactivity.

Example 2

Conjugation of Sandwich-Paired Anti-PSA MAb to Suberate Activated DNA

The labeling of sandwich paired anti-PSA monoclonal antibodies (cMAb and rMAb) has previously been reported. See U.S. patent application Ser. No. 10/701,347. In certain experiments, cMAb was labeled with single-strand DNA oligonucleotides comprising SEQ ID NO.:1, and rMAb was conjugated to either SEQ ID NO.:2 or SEQ ID NO.:3 using the methods described in U.S. patent application Ser. No. 10/701,347 (the contents of which is incorporated herein by reference in its entirety).

For the experiments of the present invention, sandwich-paired MAbs, directed against different epitopes on PSA, were obtained from BiosPacific, Inc. (Emeryville, Calif.) and each was conjugated to one of the activated overlap DNA sequences. One hundred microliters MAb (1 mg/ml) was buffer exchanged and concentrated into 0.1 M sodium phosphate, 0.15 M sodium chloride, pH 8.25 by two passes through a Microcon® 50 centrifugal ultra filtration unit (Millipore, Billerica, Mass.) at 10,000×g in a micro centrifuge at room temperature. The final volume of 25-50 μl was collected by centrifugation into a micro centrifuge tube and added to a lyophilized pellet of activated DNA (prepared as described above in Example 1). The conjugation reaction was allowed to proceed for several hours at room temperature.

The degree of antibody labeling with DNA was assessed by SDS and/or native protein gel electrophoresis. The incorporation of one or more strands of DNA into an antibody structure increased both the molecular weight and electronegativity. Antibody labeled with DNA appeared as distinct, slower migrating bands when electrophoresed on 4% polyacrylamide-SDS gels, with the rate of electrophoretic migration corresponding to the degree of DNA incorporation. The same conjugated molecules migrated faster than the corresponding underivatized antibody on 4-12% native protein gel electrophoresis. The separation was more dramatic, but less defined for higher order conjugates on native gels.

The extent of DNA conjugation varied from 50 to 100%, depending on the relative reactivity and exposure of lysine amine groups in each antibody structure. The conjugates were found to have an average labeling density of 2.5. In some experiments, the reaction mixture containing antibody-DNA conjugates was added to a second lyophilized pellet of activated DNA to increase the extent of antibody labeling with DNA.

Unreacted DNA was removed from the conjugate by FPLC gel filtration chromatography using a Sephacryl™ S-200 column (Amersham Biosciences) equilibrated with TBS, at a flow rate of 0.4 mL/min. The first eluted peaks consist of conjugated and unconjugated MAb. Pure conjugate was obtained by FPLC anion exchange chromatography using a Mono Q™ column (Amersham Biosciences) equilibrated in 20 mM Tris buffer, pH 7.4 and eluted with NaCl salt gradient (0.0-1.0 M) at a flow rate of 0.5 ml/min. MAb-DNA conjugate eluted at 60-70% salt.

The MAb-DNA conjugates were individually concentrated by centrifugal ultrafiltration and assayed for protein using a BCA Protein Assay (Pierce Biotechnology, Inc., Rockford, Ill.). Equal amounts of both conjugates were combined to form the binding pair, which hybridize to form a single molecule. Sodium azide was added to a final concentration of 0.1% and the binding pair reagent was stored at 4° C.

Example 3

Homogeneous Assay for Prostate Specific Antigen

Figure 8:
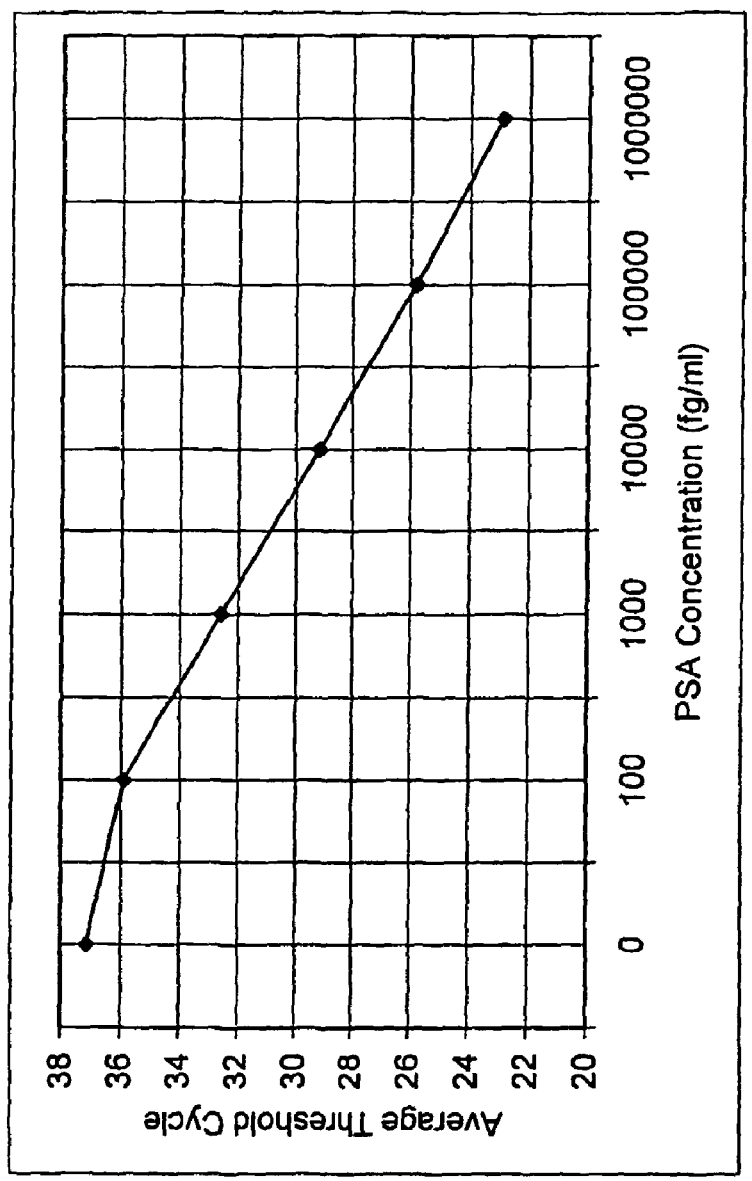
FIG. 8. shows a graph of the detection of PSA by homogeneous NADIA™

The binding pair of Example 2 was diluted to 20 pM and combined with an equal volume of a dilution series of antigen containing 0 to 1 ng/ml PSA. The antigen-binding pair mixture was incubated for two hours at 37° C. The incubation allowed formation of binding complexes comprising one antigen molecule and one binding pair molecule, with the antibody regions of each member of the binding pair bound to a distinct epitope on the PSA antigen. All salts were intentionally omitted to diminish hybridization of the overlap oligonucleotide labels in the reaction solution. Following incubation, an aliquot of the incubation mixture was removed, diluted 1:100 in 10 mM Tris, 0.1% BSA, pH 8.0 to reduce the conjugate concentration to below 1 pM and warmed for 3 min. at 45° C. The warming step effectively separated the members of the binding pair from each other by dissociating the overlap duplex regions of both uncomplexed binding members free in solution and antigen-complexed binding pairs. An equal volume of 2×PCR mix (20 mM tris-HCl, pH 8.3; 100 mM KCl; 7 mM $MgCl_2$; 400 µM each dNTP; 50 U/ml AmpliTaq® (Applied Biosystems, Foster City, Calif.) containing 400 µM of each primer (SEQ ID NOS.:4 and 5) was added. The temperature was lowered to 23° C. to preferentially reanneal DNA strands associated with analyte-binding pair complexes and initiate the first chain extension, and the reaction mixture was incubated at room temperature for 3 minutes. Under these conditions, the complementary DNA regions of complexed binding pair members re-anneal rapidly to reform the overlap hybrid of the binding pair reagent due to their close proximity and orientation. Thus, the DNA regions of complexed binding pairs can be extended by Taq polymerase, thereby forming a template for PCR. Uncomplexed, free binding pair members, however, do not re-anneal to a significant extent prior to or during the amplification reaction because they are too dilute. The reaction solution (50 µl) was transferred to the well of a microtiter plate, sealed and subjected to real-time PCR thermocycling. The temperature was ramped from 50° C. to 85° C. over 3 minutes and then held at 95° C. for 2 minutes. 45 cycles of 95° C. for 15 seconds and 62° C. for 1 minute were then performed. The results of a typical experiment are shown in FIG. 8. As shown in this Figure, a sample containing 100 fg/ml PSA was detectable over background (i.e., when compared to control samples containing no PSA).

Example 4

Homogeneous Assay for E. coli 0157

E. coli cells were obtained from ATCC (Manassas, Va.) and grown in liquid culture. Cell concentration was determined by the appearance of colonies on agar media grown overnight at 37° C.

Polyclonal antibodies against E. coli 0157 were obtained from KPL, Inc. (Gaithersburg, Md.) and conjugated to nucleic acid marker oligos having complementary overlapping sequences, according to the procedures described in Examples 1 and 2. Aliquots of the same polyclonal antibody preparation were labeled individually, each with one of the two overlap oligonucleotides, purified and combined stoichiometrically to produce a binding pair reagent.

Bacterial cells were suspended in neutral buffer (10 mM Tris, pH 7.5) to stop active growth and treated with an equal volume of 20 to 200 pM binding pair reagent for two hours at room temperature. The binding of one antibody member of the binding pair to a cell surface protein enhances the binding of the second member, forming a molecular bridge joining two adjacent binding sites on a cell. The cell suspension was then diluted 1:100 in 10 mM Tris, pH 7.5, and warmed to 45°-50° C. to dissociate excess binding pair reagent to independent binding pair members. An equal volume of 2×PCR mix containing 400 µM primers was added and the mixture incubated for 3 minutes at room temperature. The reaction (50 µl) was transferred to the well of a microtiter plate, sealed and subjected to real-time PCR under the conditions described above in Example 3. Prior to PCR, a sample was also removed for determination of bacterial cell number by plating onto solid media. Following 45 amplification cycles, a lower limit of 10-50 intact cells were detected using this method.

Example 5

Homogeneous Assay for PSA Troponin T using 3'-3' and 3'-5' Overlap of Conjugated DNA Labels Enhanced assay sensitivity may be gained by the use of binding pair reagents comprising one binding pair member composed of one DNA strand of an overlapping pair conjugated to one MAb of a sandwich pair at the 5' end as described in Example 1 and the second DNA strand conjugated to the other MAb via the 3' end. The 3' end of the 5' conjugate hybridizes to an internal sequence of the 3' conjugate, producing a binding pair where extension of the free 3' end occurs away from the center of mass of a formed complex and towards a freely rotating terminus. Such an orientation may improve the efficiency of chain extension over previously described 3'-3' overlap binding pairs by allowing for greater steric access of polymerase and the dissipation of torsional stress during initial polymerization.

The binding members of this example are formed and purified as described in Examples 1 and 2, using monoclonal antibody sandwich pair obtained from Roche Diagnostics, Indianapolis, Ind. The 5' DNA labels [SEQ ID NOS. 6 and 7] were comprised of 60 bases having the 3' terminus complimentary for 9 bases. In addition, SEQ ID NO. 6 was complimentary with an internal 9 base sequence of a 3' DNA label of 75 bases [SEQ ID NO 8]. The 3' DNA label may also be synthesized to contain one or several Spacer Phosphoramidites (Glenn Research) on the 3' end to compensate for the lost length of the binding pair crated by the internalized hybridization. SEQ ID NO. 6 was arbitrarily conjugated to monoclonial antibody designated, MAK<TNT>M-7. SEQ ID NOS. 7 and 8 were conjugated to monoclonial antibody designated, MAK<TN-T>M-11-7. The conjugation chemistry and purification remained the same.

The binding pair comprising a stable internal overlap hybrid segment is diluted, reacted with Troponin-T and amplified in the presence of downstream primers (SEQ ID NOS. 9 and 10) as described for Example 3. The free and complexed binding pair has similar melting and re-association properties as that of a 3'-3' overlap binding pair of the same sequence. The outward orientation of initial polymerization of a 3'-5-overlap improves efficiency of template sequence generation in those instances where the sandwich complex bulk may hinder the progression of the Taq polymerase. Amplification of a greater number of initial template molecules allows faster signal threshold in real-time PCR and greater assay sensitivity. The homogeneous assay for Troponin-T using a 3'-3' overlap binding pair reagent exhibited detection sensitivity similar to that of PSA (example 3). The corresponding homogeneous assay for Troponin-T using the 3'-5' overlap orientation yielded a 2-4 fold improvement.

Example 6

Homogeneous Assay for Streptavidin Using 3'-3' and 3'-5' Biotin-Labeled Overlap DNA An example of the extreme sensitivity that can be achieved in a homogeneous immuno-PCR format was demonstrated by the detection of streptavidin. Streptavidin serves as the "antigen" in this model system, having a molecular diameter of approximately 60 angstroms. The terminal amino functions of SEQ ID NOS. 6, 7 and 8 were labeled with sulfosuccinimidyl 2-(biotinamido) ethyl-1,3'dithiopropionate (Pierce Biotechnology, Inc., Rockford, Ill.) and purified by FPLC gel filtration chromatography. Each DNA label is over 200 angstroms in length when fully extended, and guarantees ability to span the distance required to achieve overlap hybridization.

Streptavidin (Prozyme, San Leandro, Calif.) was dissolved in 10 mM Tris containing 0.05% tween-20 and 0.05% sodium azide, pH 8.0 and allowed to form a complex with both 3'-3' and 3'-5' overlap DNA labeled with biotin, present at a final concentration of 10-100 pM. The complex was detected by treatment with the addition 2×PCR mix for 15 minutes, warmed to 37° C., and subjected to real-time PCR cycling in the presence of downstream primers (SEQ ID NOS. 9 and 10). Streptavidin could be detected at an input of approximately 500 molecules (50 attograms) when assayed in the 3'-5' overlap configuration and 2000 molecules in the 3'-3' orientation.

SEQ ID NO. 6
5' (C6) NH2 ATATACCCCC GCTGCCATGA TATCACTCTG
TATAAATTTG TATGCTATTC ACGATTGGGA 3'

SEQ ID NO. 7
5' (C6) NH2 ACTCTTCGCA ACAGATCCAC ACGTACACAT
CCAAACTAGC TTCCACCACC ATCCCAATCG 3'

-continued
SEQ ID NO. 8
5' ACTCTTCGCA ACAGATCCAC ACGTACGTCC CAATCGAAAG
TAAACAGTTT AAACATATGT AGCGCGTCTC CTCAT NH2 (C6) 3'

SEQ ID NO. 9
5' ATATACCCCC GCTGCCATGA TATC 3'

SEQ ID NO. 10
5' ACTCTTCGCA ACAGATCCAC ACGT 3'

Example 7

Homogeneous Assay for PSA Using 3'-5' Conjugation of Overlap DNA Labels

The binding members of this method can be formed and purified as described in Examples 1 and 2, except that one of the nucleic acids is coupled via its 3' end. The 5' DNA label is a 60 base oligonucleotide with a 3' terminus complimentary to 15 bases of an internal sequence of the 3' DNA label. The 3' DNA label is synthesized to contain spacer phosphoramidites (Glenn Research, Sterling, Va.) on the 3' end to compensate for the lost length of the binding pair created by the internalized hybridization. The conjugation chemistry and purification are performed as described above.

The binding pair comprising a stable internal overlap hybrid segment is diluted, reacted with PSA and amplified as described in Example 3. The free and complexed binding pairs have similar melting and re-association properties as 3'-3' overlapped binding pairs, which are dictated by the thermodynamic properties of DNA base-pairing. The outward orientation of initial polymerization improves efficiency of template sequence generation. Amplification of a greater number of initial template molecules allows faster signal threshold in real-time PCR and greater assay sensitivity.

Example 8

Homogeneous Assay of PSA Employing Enzymatic Digestion

Improved sensitivity for the homogeneous detection of protein antigens and microorganisms can be achieved by the use of binding members comprising antibody conjugated to single-strand nucleic acids with deoxyribose bases at the 5' end and ribose bases at the 3' end. Nucleic acid strands composed of both deoxyribose and ribose nucleotide monomer containing a 5' amino function, are synthesized by standard phosphoramidite chemistry. Alternatively, a short 3' DNA/DNA overlap may be filled in enzymatically with RNA polymerase. Overlapping nucleic acid labels made up of both DNA and RNA are synthesized starting with RNA phosphoramidite for the first 26 bases. The remaining 59 bases are synthesized with DNA phosphoramidite, terminating in a ($C_{12}$) amino function. The first 25 bases from the 5' ends represent unique primer sequences. The next 26 DNA bases are complimentary to the 26 RNA bases of the overlapping strand.

The next 9 DNA bases are complimentary to the next 9 DNA bases of the overlapping strand, thus the DNA/RNA labels are complementary on the 3' ends for the entire stretch of RNA sequence and for about 9 bases of DNA sequence. The binding pair consists of two binding members attached via a relatively lengthy stretch of DNA/RNA duplex and a relatively short stretch of DNA/DNA duplex. When conjugated to sandwich MAbs against PSA, as described in Examples 2 & 3, and combined stoichiometrically, the resulting binding pair contains a 110 base nucleotide bridge of which 60 internal bases were paired.

This reagent is used as in Example 3 to detect PSA. The binding pair forms a complex with analyte by recognition of two PSA epitopes by the two antibody members of the pair. The nucleic acid duplex region of the antigen-binding pair complex, particularly the DNA/RNA heteroduplex region, is stable at elevated temperatures and ensures the formation of a complex containing binding members locked into a specific orientation and distance from each other in the binding pair complex. Upon formation of the antigen-binding pair complex, the reaction is diluted only 10-fold and treated with RNAse H (Promega Corp., Madison, Wis.) for 30 min. at room temperature to digest the RNA strands of both the complexed and excess binding pairs, leaving a short, relatively unstable binding pair joined by the residual DNA/DNA duplex. The resulting binding pair is thermally dissociated by warming to 45° C. for 3 minutes, then cooled to room temperature. The remaining short DNA/DNA overlap reassociate rapidly, if only transiently, in the immune complex. Only the binding members fixed into position on the complex rapidly reassociate upon reducing the temperature. The dissociated binding members are unable to reform binding pairs due to their low concentration and the limited stability of the short DNA/DNA overlap. Having binding members with DNA labels of shortened 3' overlap reduces the requirement for dilution of the complex formation reaction and, therefore, improves sensitivity of the assay as compared to the assay of Example 3, above. PCR mix and primers are added, and real-time PCR amplification is performed as described above.

Example 9

Homogeneous Assay for PSA Using Enzymatic Digestion and 3'-5' Conjugation

By combining the features described above, a homogeneous assay can be devised for protein antigens and microorganism that approaches the sensitivity achieved for nucleic acid detection. The first MAb of a sandwich pair is conjugated to the 5' end of a chimeric DNA/RNA oligonucleotide. It will be appreciated that a first portion of polyclonal antibody can be used in place of the Mab. The RNA portion of the DNA/RNA oligo comprises 30 bases at the 3' end. A unique primer site is located at the 5' DNA terminus of the DNA/RNA oligo. The second Mab (which could be substituted by a second portion of polyclonal antibody) is conjugated to the 3' end of a 64-mer DNA oligonucleotide which is synthesized with several 3' phosphoramidite spacers to increase overall length. The 5' terminal 25 bases from the 5' end of the 64-mer represent a unique primer site. The next 30 bases are complimentary to the 30 RNA bases of the DNA/RNA oligo. The last 9 bases are complimentary to the DNA segment adjacent to the RNA segment (FIG. 7).

Combining both binding members produces a binding pair with an internal 9 base pair DNA/DNA hybrid adjacent to a 30 base pair DNA/DNA hybrid, as illustrated in FIG. 7. After immune complex formation, RNA digestion, melting and reannealing, the binding pair could be extended by polymerase in only one direction from the exposed 3' DNA terminus (see FIG. 7). Steric and torsional constraints imposed by 3' overlaps are eliminated, as in Example 5. Enzymatic digestion of the binding pair results in a short 9 base pair overlap, which is relatively unstable and minimizes reformation of the binding pair in the bulk solution. PCR amplification is carried out as described above.

What is claimed is:

1. A binding pair comprising:

a first binding member comprising a first antibody to an analyte coupled to the 5' end of a first single-stranded nucleic acid; and a second binding member comprising a second antibody to the analyte coupled to the 3' end of a second single-stranded nucleic acid, wherein the first antibody and second antibody form a complex with the analyte, and further wherein the first and second single-strand nucleic acids of the complex form a duplex of defined and limited stability between the terminal 3' end of the first nucleic acid and an internal sequence of the second nucleic acid; and wherein the duplex of defined and limited stability can be dissociated while the antibodies remain in place in close proximity through binding with the analyte and then reassociated to form a duplex suitable for amplification.

2. The binding pair of claim 1, wherein the first and second antibodies are monoclonal antibodies.

3. The binding pair of claim 2, wherein the first antibody and the second antibody interact independently with epitopes on the same antigen.

4. The binding pair of claim 2, wherein the first antibody and the second antibody comprise a sandwich pair.

5. The binding pair of any one of claims 1, 2, 3 or 4, wherein the first nucleic acid comprises SEQ ID NO. 1 and the second nucleic acid comprises SEQ ID NO.:2 or SEQ ID NO.:3.

6. The binding pair of any one of claims 1, 2, 3 or 4, wherein the first and second nucleic acids are each independently selected from the group consisting of DNA, RNA, and PNA.

7. The binding pair of any one of claim 1, 2, 3 or 4, wherein at least one of the first and second nucleic acids is a chimeric DNA/RNA molecule.

8. The binding pair of claim 1, wherein the nucleic acid hybrid is suitable for amplification by PCR, LCR, SDA, or TMA.

9. The binding pair of claim 1, wherein the duplex of defined and limited stability can be dissociated at a temperature between 26° C. and 45° C. while the antibodies remain in place in close proximity through binding with the analyte.

* * * * *

SEQUENCE LISTING

```
<160> NUMBER OF SEQ ID NOS: 10

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gctacggcta gatcgtgtcc atgcgcttac gacttcgatg ctcggctcgc tagctagatg    60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctccaactc ttcaacgcca tgttcttatg atacgagaga ttcagcggag gcatctagct    60

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 3
tctccaactc ttcaacgcca tgttcttatg atacgagaga ttcatcatct agctagcgag    60

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctacggcta gatcgtgtcc a                                              21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tctccaactc ttcaacgcca tgttc                                          25

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atataccccc gctgccatga tatcactctg tataaatttg tatgctattc acgattggga    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
actcttcgca acagatccac acgtacacat ccaaactagc ttccaccacc atcccaatcg    60

<210> SEQ ID NO 8
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
actcttcgca acagatccac acgtacgtcc caatcgaaag taaacagttt aaacatatgt    60
agcgcgtctc ctcat                                                     75

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic

```
                                    oligonucleotide

<400> SEQUENCE: 9
atataccccc gctgccatga tatc                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
actcttcgca acagatccac acgt                                              24
```